US008658609B2

(12) United States Patent
Marban et al.

(10) Patent No.: US 8,658,609 B2
(45) Date of Patent: Feb. 25, 2014

(54) MODULATION OF BIO-ELECTRICAL RHYTHMS VIA A NOVEL ENGINEERING APPROACH

(75) Inventors: Eduardo Marban, Beverly Hills, CA (US); Ronald A. Li, Baltimore, MD (US); Hee Cheol Cho, Columbia, MD (US); Suk-Ying Tsang, Hong Kong (CN); Tian Xue, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1550 days.

(21) Appl. No.: 11/701,985

(22) Filed: Feb. 2, 2007

(65) Prior Publication Data

US 2009/0291068 A1   Nov. 26, 2009

Related U.S. Application Data

(60) Provisional application No. 60/598,170, filed on Aug. 2, 2004.

(51) Int. Cl.
*A61K 48/00* (2006.01)
(52) U.S. Cl.
USPC ........................................ 514/44 R
(58) Field of Classification Search
None
See application file for complete search history.

(56) References Cited

U.S. PATENT DOCUMENTS

2009/0291068 A1 * 11/2009 Marban et al. ............. 424/93.21

FOREIGN PATENT DOCUMENTS

| WO | 02/098286 A2 | 12/2002 |
| WO | 2005/062958 A2 | 7/2005 |
| WO | 2006/017567 A2 | 2/2006 |
| WO | 2007/047522 A2 | 4/2007 |

OTHER PUBLICATIONS

Qu, J. et al.., "Expression and Function of a Biological Pacemaker in Canine", Circulation, Mar. 4, 2003, vol. 107: pp. 1106-1109.
Qu, J. et al., "HN2 Overexpression in Newborn and Adult Ventricular Myocytes", 2001, Circ. Res., vol. 89: pp. e8-e14.
Potapova, I., et al., "Human Mesenchymal Stem Cells as a Gene Delivery System to Create Cardiac Pacemakers", Feb. 26, 2004, Circ. Res., vol. 94: pp. 952-959.
Plotnikov, A., et al., "Biological Pacemaker Implanted in Canine Left Bundle Branch Provides Ventricular Escape Rhythms That Have Physiologically Acceptable Rates", Jan. 20, 2004, Circ. Res., vol. 109: pp. 506-512.
Accili, E., et al., "From Funny Current to HCN Channles: 20 Years of Excitation", 2002, News Physiol. Sci., vol. 17: pp. 32-27.
Lesso H et al: "Helical secondary structure of the external S3-S4 linker of pacemaker (HCN) channlels revealed by site-dependent perturbations of activation phenotype" Journal of Biological Chemistry, American Society for Biochemistry and Molecular Biology, Inc, US, vol. 278, No. 25, Jun. 20, 2003, pp. 22290-22297, XP002497948.
Tsang S Y et al: "Dissecting the structural and functional roles of the S3-S4 linker of pacemaker (hyperpolarization-activated Cyclic Nucleotide-modulate) channels by systemaive length alterations" Journal of Biological Chemistry, American Society for Biochemistry and Molecular Biology, Inc, US, vol. 279, No. 42, Oct. 15, 2004, pp. 43752-43759, XP002497946.
Tsang S Y et al: "Critical intra-linker interactions of HCN!-encoded pacemaker channels revealed by interchange of S3-S4 determinants" Biochecmical and Biophysical Research Communications, Academic Press Inc. Orlando, FL, US, vol. 322, No. 2, Sep. 17, 2004, pp. 652-658, XP004599189.
Henrikson, C. et al: "Identification of a Surface Charged Residue in the S3-S4 Linker of the Pacemaker (HCN) Channel That Influences Activation Gating" *Journal of Biological Chemistry*, vol. 278, No. 16, Apr. 18, 2003, pp. 13647-13654.
Qu, J. et al: "Functional comparison of HCN isoforms expressed in ventricular and HEK 293 cells" *Pflugers Arch—Eur J. Physiol* (2002) 444: 597-601.

* cited by examiner

*Primary Examiner* — Michael Burkhart
(74) *Attorney, Agent, or Firm* — Edwards Wildman Palmer LLP; Peter F. Corless; Alexandra J. Jones

(57) ABSTRACT

The present invention relates to novel compositions and methods to induce, and/or modulate bio-electrical rhythms (e.g. in cardiac, neuronal and pancreatic cells) by fine-tuning the activity of HCN-encoded pacemaker channels via a novel protein- and genetic-engineering approach to augment or attenuate the associated physiological responses (e.g. heart beat, neuronal firing, insulin secretion, etc) for achieving various therapeutic purposes (e.g. sick sinus syndrome, epilepsy, neuropathic pain, diabetes, etc).

14 Claims, 14 Drawing Sheets

```
                       229         237
             WT     EKGMDSEVY
        Δ 229-231   - - -MDSEVY
        Δ 229-234   - - - - - -EVY
        Δ 229-237   - - - - - - - - -
Δ 229-231/ Δ233-237 - - -M- - - - -
Δ 229-231/ Δ234-237 - - -MD - - - -
Δ 229-231/ Δ235-237 - - -MDS - - -
        Δ 232-234   EKG - - -EVY
        Δ 232-237   EKG - - - - - -
        Δ 233-237   EKGM - - - - -
        Δ 234-237   EKGMD- - - -
        Δ 235-237   EKGMDS- - -
         InsQ233Q   EKGM*Q*D*Q*SEVY
       InsQQ233QQ   EKGM*QQ*D*QQ*SEVY
     InsQQQ233QQQ   EKGM*QQQ*D*QQQ*SEVY
        237InsQQQ   EKGMDSEVY*QQQ*
       Dup229-232   EKGMDSEVY*EKGM*
       Dup229-237   EKGMDSEVY*EKGMDSEVY*
```

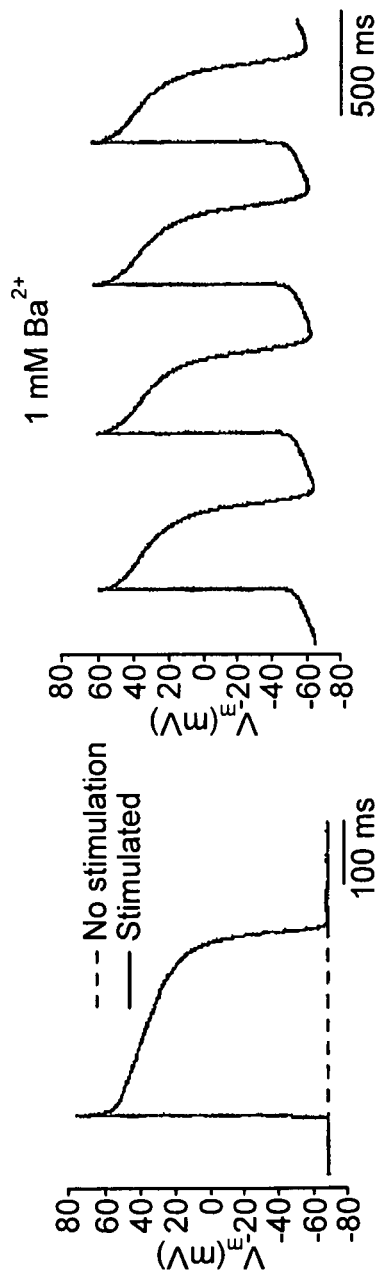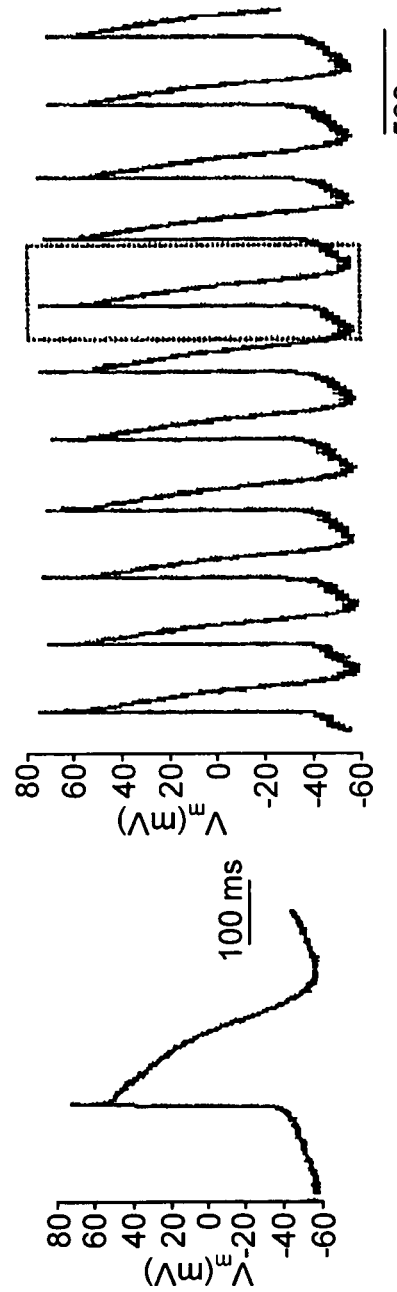
FIG. 10A
FIG. 10B

Baseline          After Isoproterenol

MODULATION OF BIO-ELECTRICAL RHYTHMS VIA A NOVEL ENGINEERING APPROACH

CROSS-REFERENCE TO RELATED APPLICATION(S)

This application is a continuation application of International Application No. PCT/US2005/027549 filed Aug. 2, 2005, which International Application claims priority from U.S. Provisional Application Ser. No. 60/598,170 filed Aug. 2, 2004, each of which applications are incorporated herein by reference in their entirety.

STATEMENT OF FEDERALLY SPONSORED RESEARCH

Funding for the present invention was provided in part by the Government of the United States by virtue of Grant No. HL72857 by the National Institutes of Health. Thus, the Government of the United States has certain rights in and to the invention claimed herein.

FIELD OF THE INVENTION

The present invention relates to novel approaches for engineering the generation of bioelectrical impulses (such as those from the cardiac, neuronal and pancreatic cells, etc) using genetically-modified membrane channels.

BACKGROUND OF THE INVENTION

Spontaneous cellular electrical rhythms (or pacing) govern numerous biological processes from the autonomous beating of the heart, pain transmission, to respiratory rhythms and insulin secretion. For instance, spontaneous neuronal electrical discharges in damaged dorsal root ganglions underlie neuropathic pain but limited useful therapy is available. Recently, we have also discovered that key ionic components which underlie the electrical rhythms in pancreatic β cells also modulate the secretion of insulin. In the heart, abnormal pacing leads to various forms of arrhythmias and electrical disorders that necessitate traditional pharmacologic interventions and implantation of costly electronic devices that are associated with various side effects, inherent risks, and expenses.

Autonomous rhythmic heart beats are modulated by sympathetic and parasympathetic means according to everyday needs; such normal rhythms originate in the sino-atrial (SA) node of the heart, a specialized cardiac tissue consisting of a few thousands pacemaker cells that spontaneously generate rhythmic action potentials (AP) (i.e. pacing). One of the key players known to prominently modulate the pacing activity of SA nodal cells is the cardiac membrane current $I_f$ ("f" for funny), a depolarizing, mixed $Na^+/K^+$ inward current[1]. Despite the fact that $I_f$ has been recognized for over 20 years, the encoding genes, collectively known as the hyperpolarization-activated cyclic-nucleotide-modulated (HCN) channel gene family, have been cloned relatively recently.[2-4] To date, four isoforms, namely HCN1-4, each with a distinct pattern of tissue distribution and biophysical profiles, have been identified[3-8]. Of the two predominant isoforms in the SA node, time-dependent HCN1 currents open ~40 times faster than those of HCN4 channels[9-13]; a single base-pair deletion mutation detected in the human HCN4 gene of a patient has been linked to idiopathic sinus node dysfunction[14].

Since HCN1-4 readily co-assemble to form heterotetrameric complexes with context-dependent properties that can not be predicted from the individual isoforms[15-18], native $I_f$ can have complex molecular identity depending upon the particular isoforms expressed. Furthermore, HCN channels activate more positively in native cardiomyocytes than in mammalian expression systems, suggesting that the gating properties of $I_f$ are highly context-dependent (Qu et al 2002 Pflugers) (e.g. the presence of endogenous subunits). Thus, native $I_f$ is difficult to reproduce by simple expression of a single HCN isoform. Indeed, previous attempts to overexpress wild-type HCN2 in adult ventricular cardiomyocytes failed to induce automaticity[19], presumably due to its negative activation relative to the voltage range of cardiac pacing. It would be highly desirable to develop a flexible and effective approach that enables us to delicately customize the activity of HCN channels so as to achieve a range of therapeutic outcomes. For instance, to engineer a HCN channel construct, which opens more readily than wild-type HCN channels (and thereby compensates the context-dependent negative activation shift in heart cells) to better mimic native nodal $I_f$ so as to effectively induce or modulate cardiac automaticity. The same principle can be extrapolated for application in other cell types whose functions depend on electrical rhythms.

As previously mentioned, HCN-encoded $I_f$ (or $I_h$) plays an important role in the spontaneous rhythmic activity in cardiac, neuronal as well as insulin-secreting cells (32-38). Although classical depolarization-activated voltage-gated $K^+$ ($K_v$) and HCN channels are structurally homologous to each other, the latter are uniquely distinctive from the $K_v$ counterparts by their signature 'backward' gating (i.e. activation upon hyperpolarization rather than depolarization). The basis of HCN gating is largely unknown.

Recent evidence suggests that the voltage-sensing mechanisms of HCN and $K_v$ channels are conserved despite their opposite gating behaviors (i.e. the HCN S4 also moves outward and inward during depolarization and hyperpolarization, respectively) (39, 40). This finding raises the possibility that the S3-S4 linker (defined as residues 229EKGMD-SEVY237 of HCN1; FIG. 1), which is directly tethered to the S4 voltage-sensor, also influences the activation phenotypes of HCN channels as does that of $K_v$ channels (41-43). Indeed, we have recently reported that the S3-S4 linker contains several functionally-important residues (44, 45). For instance, single alanine substitutions of G213, M232 and E235 produced depolarizing activation shifts. The pattern of site-dependent perturbations of HCN activation, along with computational modeling, further suggests that part of the linker conforms a helical secondary structure with the determinants G231, M232 and E235 clustered on one side. It would be desirable to understand the structural and functional roles of the HCN S3-S4 linker. Such understanding would be helpful in developing engineered HCN channels which would open more (or less) readily for increasing (or decreasing) automaticity in cardiac, neuronal, pancreatic cells, etc.

Throughout this application, various publications are referenced to by numbers. Full citations for these publications may be found at the end of the specification immediately following the Abstract. The disclosures of these publications in their entireties are hereby incorporated by reference into this application in order to more fully describe the state of the art to those skilled therein as of the date of the invention described and claimed herein.

SUMMARY OF THE INVENTION

Here we have conceived of a novel method to modulate or "custom-tailor" bio-electrical rhythms in such specialized cells as cardiac, neuronal and pancreatic cells, by targeting the activity of particular ion channels using a novel protein- and genetic-engineering combined approach. In combination with protein engineering, this can be accomplished by in vivo or ex vivo gene transfer of specific normal and/or engineered ion channel proteins into native tissues or stem cell-derived derivatives (followed by cell transplantation), respectively, to produce the desired physiological consequences in vivo. For instance, one can first engineer HCN channels such that their activation thresholds are shifted either above or below that of normal channels by a given level. Such genetically engineered recombinant constructs, when introduced into cells, can alter the associated bio-electrical rhythmic activity and subsequently augment or attenuate their physiological responses (e.g. heart beat, the feeling of pain, appetite, insulin secretion, etc). Collectively, our approach may lead to new effective therapies for such clinical problems as arrhythmias (sick sinus syndrome), epilepsy, neuropathic pain, obesity, diabetes, etc. The efficacy of this approach has been verified by our in vivo gene transfer experiments, in the context of the heart, to correct an arrhythmias (sick sinus syndrome) described in the paragraphs that follow.

We now provide gene transfer and cell administration methods that can create a "bio-battery" to exert pacemaking function, and/or to modulate the activity of an endogenous or induced cardiac pacemaker function using genetically modified HCN constructs.

Methods of the invention using genetically modified HCN constructs may be employed to create and/or modulate the rhythmic activity of an endogenous pacemaker (such as the sinotrial node of a mammalian heart, neuronal cells of the central nervous system, β-cells of the pancreas, etc) and/or an induced pacemaker (e.g. biological pacemaker generated from stem cells or converted electrically-quiescent cells).

More particularly, in a preferred aspect of the invention, quiescent heart muscle cells are converted into pacemaker cells by in vivo viral gene transfer or modified cell transfer (e.g., differentiated stem cells).

In a further aspect, a composition is administered to a subject to alter the frequency of (i.e. to tune) an existing endogenous or induced cardiac pacemaker function. Polynucleotides of or modified cells containing a genetically modified HCN construct that displays a particular phenotype are preferred agents for administration. The method can be applied to virtually any cell types that exhibit bioelectrical rhythms (e.g. certain neuronal and pancreatic cells) other than cardiac cells so as to subsequently modify/improve their physiological functions. For instance, the activity of electrically active neuronal cells in the case of neuropathic pain can be decreased using a different HCN construct (e.g. one that is less ready for opening or even a dominant-negative construct) to reduce or eliminate the sensation of pain. (i.e. to correct a particular defect due to diseases or traumas).

Specifically, the present application discloses that the length of the HCN1 S3-S4 linker is a determinant of gating. Systematic alteration of the linker length by deletion and insertion, followed by detailed characterization of the associated functional consequences, revealed that the linker length and its amino acid constituents prominently modulate gating properties in a systematic pattern. However, the major principle is that other functional HCN domains (e.g. S4 and the pore region that affect gating properties, the cAMP binding domain, etc) can be similarly modified to achieve a particular outcome.

Other aspects of the invention are discussed infra.

BRIEF DESCRIPTION OF THE FIGURES

FIG. 10, A and B are representative illustrations demonstrating the effects of $I_{K1}$ suppression.

DETAILED DESCRIPTION OF THE INVENTION

Figures 1A, 1B:
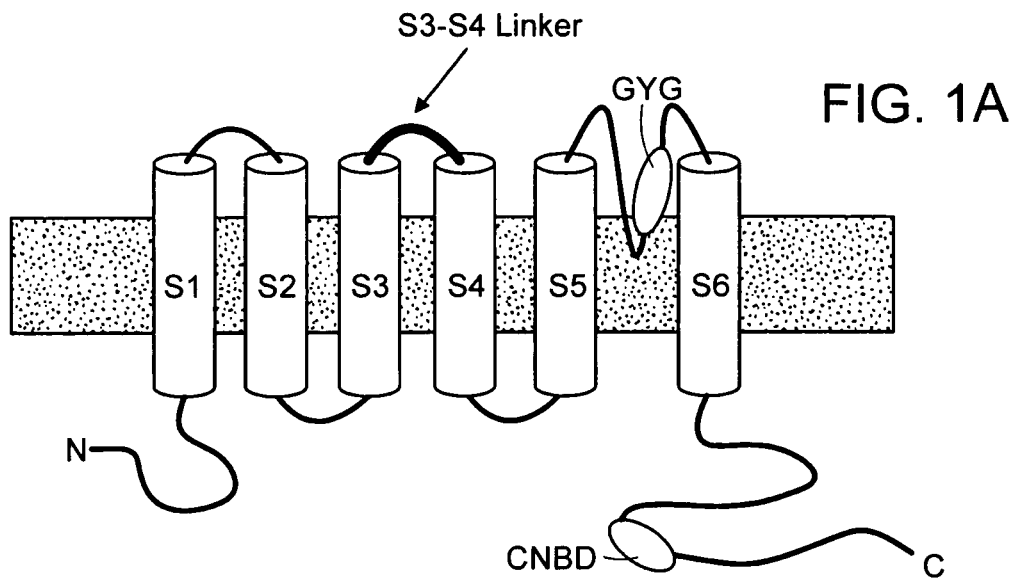
FIG. 1 represents illustrations of the putative transmembrane topology of HCN1 wherein A) The six putative transmembrane segments (S1-S6) of a monomeric HCN1 subunit. The S3-S4 linker is thickened; B) S3-S4 linker sequences of WT HCN1 and other channel constructs investigated in the present study. Functional and non-functional constructs are labeled green and purple, respectively. M232 is highlighted in red.

The present application discloses that overexpression of a single engineered HCN construct that mimics the positive activation profile of native nodal $I_f$ enables the conversion of normally-quiescent ventricular cardiomyocytes to rhythmic pacemaker-like cells (even without, and is superior to the outcome of $I_{K1}$ inhibition). These results infer that $I_f$ is indeed a crucial oscillator of the membrane potential. This finding provides new insights into the functional role of $I_f$ in pacing (cardiac, neuronal and pancreatic). To date, at least three approaches have been taken to induce ectopic pacemaker activity in the heart. These include overexpression of $\beta_2$-adrenergic receptor in the atria[30] and genetic suppression of ventricular $I_{K1}$[21,22]. Specifically, somatic gene transfer of the dominant-negative construct Kir2.1-AAA in adult guinea pig ventricular myocytes suppressed $I_{K1}$ expression (by ~80%), leading to the conversion of quiescent ventricular muscle cells into spontaneously-active "pacemaker-like" cells in a manner analogous to the Ad-HCN1-$\Delta\Delta\Delta$-transduced cells described in this study. However, Kir2.1AAA-induced ventricular automaticity, similar to that caused by $Ba^{2+}$ blockade of $I_{K1}$, was much slower than the normal heart rate. In other words, $I_{K1}$ suppression by Kir2.1-AAA acts as a simple on-and-off switch to unleash latent pacemaking activity of otherwise quiescent ventricular cells. However, it does not provide a direct means to modulate the induced firing activity. Our present results implicates that ectopic cardiac pacing can be better achieved by modulating a genuine pacemaker current—$I_f$, rather than suppressing the inhibitor $I_{K1}$.

Previous attempts to reproduce nodal $I_f$ in ventricular myocytes by overexpressing WT HCN2 alone, however, failed to induce automaticity[28]. By contrast overexpression of the same channels in the left atrium or the left bundle branch could induce pacemaking function but only after vagal stimulation-induced sinus arrest[19], limiting any potential useful therapeutic applications. Since $I_{K1}$ and $I_f$ stabilizer and oscillator of the membrane potential, are presumed to oppose each other, the differences observed in these experiments could be attributed to the higher expression levels of $I_{K1}$ in the ventricles than in the atria[31]. It is also likely that the $V_{1/2}$ and/or the magnitude of the expressed $I_f$ in these HCN2 experiments (−96 mV and ~0.8 pA/pF vs. 53.8 mV and 8.2±1.4 pA/pF at −140 mV in our case) were below the thresholds required to cause active pacing in the presence of $I_{K1}$, a notion supported by our present results (see later)

Interestingly, $I_f$ overexpression induces a faster pacing rate without $Ba^{2+}$ block of $I_{K1}$. Perhaps, $I_{K1}$ hyperpolarizes the MDP, resulting in a higher probability of opening of the hyperpolarization-activated $I_f$ during early phase-4 depolarization. Therefore, the approaches of $I_f$ overexpression and $I_{K1}$ suppression to induce pacing are not necessarily synergistic. Rather, the functional effects of $I_f$ on pacing are the function of a number of cellular parameters (such as MDP and $I_{K1}$) as well as its own properties (conductance, gating properties, etc). The data presented in this application provides a pragmatic platform for using engineered HCN constructs that exhibit specific biophysical properties to construct a library of engineered gene- or cell-based (e.g. ex vivo adult or embryonic stem cell-derived) bio-batteries (or pacemaker) with a range of customized basal oscillation frequency.

Previous studies of $K^+$ channels have shown that the length of their S3-S4 linker is a determinant of gating kinetics (41-43). Complete deletion of S3-S4 linker in $K_v$ channel still yielded robust $K^+$ current (42), suggesting that the linker probably does not participate in large conformational changes during channel activation (42, 43). This in turn implies that during activation of $K_v$ channels, either the S4 voltage sensor moves only a short distance or the S3-S4 linker can move along with S4 (cf. paddle model, reference 48; see later). Despite these studies of $K_v$ channels, the role of the S3-S4 linker length in HCN channel functions has not been fully elucidated. Our data suggest that shortening the linker in deletion mutant $\Delta 235$-237 caused depolarizing activation shift and slowed kinetics that could not be explained by removing the charge at position 235 alone (44, 45). Given HCN and $K_v$ channels are structurally analogous, this finding motivated us to investigate in details the role of the S3-S4 linker length in HCN functions. Indeed, we found that both the length and composition of the S3-S4 linker prominently influence HCN gating, making this region a prime candidate for modulating HCN channel activity (for subsequent tissue-engineering).

The S3-S4 linker, directly tethered to the S4 voltage sensor, may influence the energy barriers that separate the channel transitions required for channel openings by undergoing a series of conformational changes during the gating process. Our data show that shortening and prolonging the S3-S4 linker generally shifted the steady-state activation positively and negatively, implying that short linkers generally promote HCN channel activation (only if a critical length is met and that the shortened linker also contains the critical determinant M232) whereas long linkers likely restrict channel activation. Several deletion and insertion constructs displayed substantial changes in gating kinetic while having relatively modest alterations in their steady-state activation properties. Perhaps, changing the linker length alter the transitions among different channel conformations that occur during the process of activation. Indeed, the linker may either affect the rate at which S4 voltage sensor response to the change in membrane potential, or affect conformational changes that occur after S4 has responded to the changes in membrane potential. Disregarding the sequence, these results hint at a possible role of the S3-S4 linker in establishing the time scale of HCN channel activation, as previously proposed for L-type $Ca^{2+}$ channels (49).

Interestingly, $\Delta 234$-237 nearly restores normal HCN1 gating properties with $V_{1/2}$, activation and deactivation kinetics indistinguishable from those of WT. Based on our previously proposed model (i.e. residues 231-237 conform a helical arrangement with Glu-229 and Lys-230 forming a coil structure that connects the S3-S4 linker to S3)(14), $\Delta 234$-237 is predicted to contain one helical turn. Coincidentally, a S3-S4 linker consisting of only 3 amino acids (i.e. one helical turn) is also sufficient to restore WT activation phenotype for Shaker $K^+$ channels (12). Although $V_{1/2}$ of $\Delta 34$-237 was statistically indistinguishable from that of WT (p>0.05), activation was modestly shifted in the depolarizing direction, presumably as a result of the deletion of E235, which is known to influence activation gating by acting as a surface charge (44).

Another feature of the HCN1 S3-S4 linker is that M232 but not other linker residues is prerequisite for channels to function. We have previously demonstrated that alanine substitution of residue 232 significantly altered gating (45). When substituted by an alanine (i.e. M232A), activation is shifted in the depolarizing direction and gating kinetics are decelerated. The present findings further suggest that the presence of M232 may be critical for maintaining the structural integrity of the S4 voltage sensor. Consistent with the latter possibility, non-functional constructs such as Δ229-234, Δ229-237, Δ232-234 and Δ232-237 have their N-terminal S4 segments (residues 238 to 240) changed from the original helical conformation to a coiled structure based on the predictions generated by the modeling algorithm SSpro2 (data not shown). In contrast, constructs that express robust currents (e.g. Δ229-231, Δ234-237 and InsQQQ233QQQ) have intact helical not different from that of WT. Alternatively, it is also possible that without M232, S4 can no longer move properly in response to voltage changes or its movements cannot lead to subsequent channel openings. Observations with Δ229-231/Δ233-237, Δ229-231/Δ234-237 and Δ229-231/Δ235-237 also suggest that even very short S3-S4 linkers enable sufficient displacements of the S4 voltage sensor that are required for HCN channel opening.

HCN Channels:

A particular class of ion channels, namely the HCN channel family, prominently modulates the rhythmic electrical activities in the heart, the pancreas and the CNS by determining their frequency of oscillations. An "HCN channel" is a sodium/potassium permeable cation channel that is activated by membrane hyperpolarisation and modulated by cAMP and cGMP. Activation of HCN channels will typically lead to the development of an inward current carried by sodium/potassium which causes depolarisation of the membrane potential.

We have designed a flexible and effective approach that enables us to delicately customize the activity of HCN channels. For instance, we have engineered HCN channels such that their activation thresholds are shifted either above or below that of normal channels (cf. FIG. 8). Such genetic recombinant constructs, when introduced into cells, can alter the associated bio-electrical rhythmic activity and subsequently augment or attenuate their physiological responses. The efficacy of this approach has been verified by our in vivo gene transfer experiments. Although previous attempts to overexpress HCN2 channels in ventricular cardiomyocytes failed to induce automaticity, we have successfully implanted an active biological oscillator of the membrane potential (i.e. a self-renewable bio-battery) into cardiac muscle cells via somatic gene transfer of a recombinant HCN construct (i.e. HCN1-EVY235-7ΔΔΔ in the specific example provided), whose activation threshold is ~20 mV lower than wild-type channels to favor channel opening. The result was the remarkable conversion of quiescent cardiac muscle cells into spontaneously-active "pacemaker" cells. Unlike genetic suppression of Kir2-encoded $I_{K1}$, which is merely an on-and-off switch which does not provide a direct means to modulate the induced pacing rate, HCN genes are genuine pacemaker genes that can be used to induce, as well as to modulate and customize pacing (i.e. analogous to an on-and-off dimmer switch). The strategy can be similarly applied to such electrically-active cell as neuronal and pancreatic cells to modulate their physiological functions. Collectively, our results might lead to novel approaches for engineering bio-electrical rhythms (e.g. gene- or cell-based biological pacemakers with customized firing rates, and for novel pain managements, promoting insulin secretion, etc).

As mentioned, modified cells containing a genetically modified HCN construct also may be administered to induce or modulate pacemaker to cells or a subject. For instance, the administered modified cells suitably may be cardiomyocytes that can provide pacemaker function and have been differentiated from stems cells such as pluripotent embryonic stem cells (or other multipotent stem cells). The latter may be stem cell-derived pacemaker cells (by spontaneous and/or driven differentiation) and/or stem cell-derived myocytes (e.g. ventricular cells) that have been converted to provide pacemaker function. As referred to herein, the administered cells preferably are modified prior to administration, such as stem-cell-derived cardiomyocytes or cardiomyocytes that are transformed with an expression system such as those disclosed herein.

Gene expression of a genetically modified construct of HCN may be promoted by administering an appropriate polynucleotide compound to a mammal. We have particularly found that HCN activity can be modulated in both positive and negative directions such that their activation thresholds can be shifted to a desired level. Hence, cardiac pacing, and subsequent heart rate, or neuronal and pancreatic pacing, can be effectively modulated (both increase and decrease) by such control of HCN gene expression. For instance, pacing can be decelerated by inhibiting the endogenous HCN channel activity and/or by shifting the activation threshold above the endogenous level (alternatively, acceleration can be achieved by increasing the numbers of operating channels via overexpression and/or by shifting the activation threshold below the endogenous level). Similarly, the response of the native pacemakers to the secondary messenger cAMP also can be modulated, e.g. by using engineered channels of given sensitivities.

The administered polynucleotide of a genetically modified construct of HCN suitably induces or modulates (increase or decrease) at least one electrical property. In the heart for example, preferred use of the invention modulates electrical conduction and preferably can reconfigure all or part of the cardiac action potential (AP). That use helps achieve a desired therapeutic outcome. Significant disruption of normal electrical function is usually reduced and often avoided by the present methods.

Preferably, administration of a polynucleotide or modified cells to cells in accordance with the invention will provide a discernable difference (increase or decrease) in the rate of electrical signal output (firing rate) of the treated myocardial, neuronal, pancreatic cells, etc. More particularly, preferably the administration provides at least about a 2, 3, 4 or 5 percent increase or decrease, more preferably at least about a 10, 15, 20, 25, 30, 40, 50 or 100 percent (increase or decrease) in the firing rate of the treated cells. Firing rate of treated cells may be determined by standard procedures, particularly by a standard electrophysiological assay as such assay is defined below Examples of preferred administration routes, polynucleotides are provided in the discussion that follows. In general, polynucleotide expression conducive to using the invention is apparent as a shift in a recording (relative to baseline) obtained from at least one of the standard electrophysiological assays. Preferably, administration of a polynucleotide in accordance with the invention provides an increase or decrease of an electrical property by at least about 10% relative to a baseline function. More preferably, the increase or decrease is at least about 20%, more preferably at least about 30% to about 50% or more. That baseline function can be readily ascertained e.g. by performing the electrophysiological assay on a particular mammal prior to conducting the invention methods. Alternatively, related baseline function can be determined by performing a parallel experiment in which a control polynucleotide is administered instead of the polynucleotide of interest. It will be apparent that once a reliable baseline function has been established (or is available from public sources), determination of the baseline function by the practitioner may not always be necessary. Examples of relevant electrical properties are known and include, but are not limited to, at least one of firing rate, refractoriness, conduction velocity, focal automaticity, and spatial excitation pattern. Heart or contraction rate (firing rate) or pulse rate is preferably evaluated.

By modulating cardiac contraction rate, the invention can be employed to treat or prevent (prophylactic treatment) a wide range of cardiac related diseases and disorders. For example, methods of the invention will be useful for treatment of subjects suffering from or susceptible to cardiac related syncope, particularly Stokes-Adam syncope. Methods of the invention also will be useful to treat subjects suffering from or susceptible to various abnormalities of sinus node function, including persistent sinus bradycardia, sino-atrial (S-A) block manifested as S-A Wenckebach, complete S-A block or sinus arrest (sinus impulse fails to activate the atria), and high-grade atriventricular block. Methods of the invention also will be useful to treat subjects suffering from or susceptible to bradycardia-tachycardia syndrome, bradycardia of other causes. Excitability diseases other than those of the heart such as neuropathic pain, epilepsy, muscle myotonias, diabetes, obesity that involve bioelectrical rhythms can also be treated.

Therapeutic methods of the invention generally comprise administration of an effective amount of firing rate modulating polynucleotide or modified cells containing the genetically modified construct of HCN1 to a mammal in accordance with the invention. The administration is preferably localized within targeted areas of the tissue of interest of the mammal to avoid e.g. toxicity. Such administration is suitably accomplished by injection, catheter delivery and other means as disclosed e.g. herein. Preferably, the mammal is first identified and selected for the treatment and then the therapeutic composition is administered. For instance, a mammal can be identified that is suffering from or susceptible to a disease or disorder as disclosed herein such as a cardiac-related syncope, particularly Stokes-Adam syncope; an abnormality of sinus node function such as persistent sinus bradycardia, sino-atrial (S-A) block manifested as S-A Wenckebach, complete S-A block or sinus arrest, and high-grade atriventricular block; or bradycardia-tachycardia syndrome or other bradycardia related condition.

In another aspect, the invention provides a kit for performing one or a combination of the invention methods disclosed herein. Preferably, the kit includes at least one suitable myocardium nucleic acid delivery system and preferably at least one desired polynucleotide and/or modified cell containing the genetically modified construct of HCN1. Preferably, that polynucleotide is operably linked to the system i.e., it is in functional and/or physical association therewith sufficient to provide for good administration of the polynucleotide into the heart. Additionally preferred kits include means for administering the polynucleotide or modified cells containing the genetically modified construct of HCN to a mammal such as a syringe, catheter and the like.

All publications and patent applications cited in this specification are herein incorporated by reference as if each individual publication or patent application were specifically and individually indicated to be incorporated by reference.

EXEMPLIFICATION

Materials and Methods for Examples 1 thru 3

Molecular Biology, Adenoviral Transduction, and Myocyte Isolation.

PCR-based mutagenesis of rbHCN1 (generously provided by Dr. H. Ohmori, Kyoto University, Japan) was performed with overlapping oligos as described in our previous publications[23,24]. HCN1-ΔΔΔ was subcloned into the bicistronic adenoviral vector pAdCMV-GFP-IRES or pAd-CGI[25] to create pAdCGI-HCN1-ΔΔΔ. Adenoviruses were generated by Cre-lox recombination of purified ψ5 viral DNA and shuttle vector DNA as previously described[26]. The recombinant products were plaque purified, yielding concentrations of the order of $10^{10}$ plaque-forming units (PFU) ml$^{-1}$, followed by injection into the left ventricular cavity of anesthetized guinea-pigs during transient cross-clamping of the great vessels. Left ventricular cardiomyocytes were isolated enzymatically 72-94 hours after in vivo transduction for electrophysiological recordings. Transduction efficiency, as determined by GFP epifluorescence, was typically about 20%.

Electrophysiology

Electrical recordings were performed using the whole-cell patch-clamp technique[27] with an integrating amplifier. Pipettes had tip resistances of 1-3 MΩ when filled with an internal solution containing (mM): KCl, 140; ATP (magnesium salt), 4; EGTA, 5; MgCl$_2$, 1; and Hepes, 10; pH 7.4. The external bath solution was composed of (mM): N-methyl-D-glucamine, 140; KCl, 5.4; glucose, 10; MgCl$_2$, 1; CaCl$_2$, 0.1; CdCl$_2$, 0.5; 4-aminopyridine, 5; and Hepes, 10; pH 7.4. All recordings were performed at room temperature (~23° C.). Data reported are means±S.E.M. with P<0.05 indicating statistical significance.

Swine Sick Sinus Syndrome Model and Gene Transfer.

Anesthesia of miniswine (45-55 kg) was performed by intravenous injection of propofol and isoflurane (1%) with intubation and mechanical ventilation. After obtaining vascular access via femoral venous cutdown, a 7F electrophysiological catheter (Biosense—Weber, Calif., USA) was introduced into the RA and navigated to the SA node located between the junction of superior vena cava and high right atrium to deliver radiofrequency energy, generated using a Stockert 70 RF generator (Biosense—Webster, Calif.) with the temperature control mode and maximum output set to 50° C. and 35 Watt, respectively, at sites with the earliest endocardial activation during sinus rhythm to cause sinus dysfunction. After ablation, we implanted a dual-chamber pacemaker (Medtronic Inc. or Guidant Corp) with one electrode positioned at the high anterolateral wall of the RA and another at the right ventricular apex to provide supportive pacing if the heart rate fell below 60 bpm. Through a left thoracotomy, pAdCGI-HCN1-ΔΔΔ (2×$10^{10}$ PFU) or saline (2-3 ml) was injected in the LA appendage. A metal clip was used to mark the injection site.

Electroanatomic Mapping 10 to 14 days after the injection procedure, we assessed the endocardial activation patterns SSS animals by electroanatomical mapping of the atria. A non-fluoroscopic magnetic electroanatomic system (CARTO; Biosense Webster) which utilizes a special mapping catheter (NAVI-STAR; Biosense Webster) to collect the spatial distribution of local endocardial activation times relative to a reference electrogram using a magnetic technology, was employed as previously described (Ben-Haim, 1996 #388). By moving the mapping catheter to different locations in the RA and LA during spontaneous or atrial pacing rhythm, a color coded three-dimensional endocardial activation map was constructed (red, the earliest activation site; purple, the latest). The normal sinus rhythm of non-ablated animals was also mapped as controls.

Materials and Methods for Examples 4 thru 8

Molecular Biology and Heterologous Expression

Murine HCN1 (kindly provided by Drs. Siegelbaum and Santoro) was subcloned into the pGHE expression vector (16). Mutations were created using PCR with overlapping mutagenic primers. The desired mutations were confirmed by DNA sequencing. cRNA was transcribed from NheI-linearized DNA using T7 RNA polymerase (Promega, Madison, Wis.). HCN1 channel constructs were heterologously expressed and studied in *Xenopus* oocytes. Stage IV-VI oocytes were surgically removed from female frogs anesthetized by immersion in 0.3% 3-aminobenzoic acid ethyl ester, followed by digestion with 1.5 mg/ml collagenase (type IA) in OR-2 solution containing 88 mM NaCl, 2 mM KCl, 1 mM $MgCl_2$, and 5 mM HEPES (pH 7.6) for 30-40 min. Defolliculation was performed by incubating cells in ND-96 solution containing 96 mM NaCl, 2 mM KCl 1.8 mM $CaCl_2$, 1 mM $MgCl_2$, and 5 mM HEPES (pH 7.6) with 10% fetal bovine serum for 15-30 min. Isolated oocytes were injected with cRNA (50 ng/cell) and stored in 96 mM NaCl, 2 mM KCl, 1.8 mM $CaCl_2$, 1 mM $MgCl_2$, and 5 mM HEPES (pH 7.6) for 1-2 days at room temperature for protein expression before electrical recordings.

HCN1-GFP Fusion Constructs and Heterologous Expression in TsA-201 Cells

HCN1-GFP and HCN1Δ232-234-GFP were subcloned into into the mammalian expression vector pCI, followed by transfecting into tsA-201 cells using LipofectAMINE Plus 2000 (Invitrogen, Carlsbad, Calif.) according to the manufacturer's protocol. Transfected cells were trypsinized and plated on glass-bottom culture dishes (MatTek Corporation, Ashland, Mass.) 4 hours before confocal microscopy (UltraView Confocal Imaging System, PerkinElmer Life Sciences) with an excitation wavelength of 488 nm.

Electrophysiology

Two-electrode voltage-clamp recordings were performed at room temperature using a Warner OC-725B amplifier. Agarose-plugged electrodes (TW120-6, World Precision Instruments, Inc., Sarasota, Fla.) were pulled using a Narishige PP-83 vertical puller, with final tip resistances of 2-4 megaohms when filled with 3 M KCl. The recording bath solution contained 96 mM KCl, 2 mM NaCl, 10 mM HEPES, and 2 mM $MgCl_2$ (pH 7.6).

Experimental Protocols and Data Analysis

The steady-state current-voltage (I-V) relationship was determined by plotting the HCN1 currents measured at the end of a 3-s pulse ranging from −140 to 0 mV from a holding potential of −30 mV against the test potentials. Currents were normalized to the maximum average current recorded in WT channels.

The voltage dependence of HCN channel activation was assessed by plotting tail currents measured immediately after pulsing to −140 mV as a function of the preceding 3-s test pulse normalized to the maximum tail current recorded. Data was fit to the Boltzmann functions using the Marquardt-Levenberg algorithm in a nonlinear least-squares procedure:

$$m_\infty = 1/(1+\exp((V_t - V_{1/2})/k)),$$

where $V_t$ is the test potential; $V_{1/2}$ is the half-point of the relationship; k=RT/zF is the slope factor, and R, T, z, and F have their usual meanings.

For simplicity, the time constants for activation ($\tau_{act}$) and deactivation ($\tau_{deact}$) were estimated by fitting macroscopic and tail currents with monoexponential function although sigmoidicity with an initial delay was observed before the onset of HCN1 currents at some voltages. The mechanism underlying such complex kinetic behavior of HCN channels is not understood. Further analysis using multiple exponential components is beyond the scope of this work.

Data was presented as means±S.E. Statistical significance was determined for individual data points and fitting parameters using one-way analysis of variance and the Tukey HSD post-hoc test at 5% level.

EXAMPLES

Example 1

Expression of an Engineered $I_f$ in Ventricular Cardiomyocytes

We first created the recombinant adenoviruses Ad-CGI and Ad-CGI-HCN1-ΔΔΔ to overexpress the green fluorescent protein (GFP) and the engineered HCN1 construct EVY235-7ΔΔΔ, respectively. HCN1-EVY235-7ΔΔΔ channels, whose S3-S4 linker has been shortened by deleting residues 235-237, was chosen because they open more readily (with a ~20 mV depolarizing shift of activation $V_{1/2}$) than any of the wild-type HCN1-4 isoforms when expressed in heterologous expression systems[23,24]. Therefore, we conjectured that overexpressing EVY235-7ΔΔΔ channels alone in cardiomyocytes would sufficiently mimic the heteromultimeric native nodal $I_f$ without having to simultaneously express or manipulate multiple HCN isoforms.

FIG. 9 shows that $I_{K1}$ (A and E), which could be completely blocked by 1 mM $Ba^{2+}$ (B and F) was robustly expressed in control (non- or Ad-CGI-transduced) adult guinea pig left ventricular (LV) cardiomyocytes (n=36). For LV cells isolated from animals 72-96 hours after in vivo gene transfer of Ad-CGI-HCN1-ΔΔΔ via intra-cardiac injection, a similar $Ba^{2+}$-sensitive $I_{K1}$ with properties not different from those of control cells was also expressed (FIGS. 9C & E; p>0.05). By contrast, a time-dependent current component, reminiscent of nodal $I_f$, could be recorded after 1 mM $Ba^{2+}$ subtraction (n=6; FIG. 9D). This Ad-CGI-HCN1-ΔΔΔ-induced $I_f$-like component, sensitive to the known HCN blocker $Cs^+$ or ZD7288 (data not shown), increased in magnitude and became faster with progressive hyperpolarization (FIGS. 9F-G). The midpoint ($V_{1/2}$) and slope factor (k) derived from the steady-state activation curve were −61.9±1.6 mV and 9.7±1.0, respectively (FIG. 9H). Taken collectively, Ad-CGI-HCN1-ΔΔΔ-induced $I_f$, unlike that mediated by HCN2-overexpression alone in the ventricle which activated more slowly (by ~10-fold) and negatively ($V_{1/2}$, ~82 mV), had properties that largely resemble those of endogenous heteromultimeric $I_f$ in genuine pacemaker cells.

Example 2

Induced Automaticity by HCN-Encoded $I_f$ Overexpression

Shown in FIG. 10A (left) is a typical control ventricular cell (same from FIGS. 9A-B) that was normally electrically-quiescent with no spontaneous activity. The resting membrane potential, RMP, was −76±5 mV (n=7). Upon injection of a stimulating current (~0.8 nA for 5 ms), the same cell generated a single action potential (AP), indicating normal excitability. Addition of 1 mM Ba$^{2+}$ to block I$_{K1}$ destabilized the normal RMP and subsequently resulted in spontaneous firing with an average cycle length of 689±132 ms that was ~3-fold slower than that of guinea pig nodal cells (FIG. 10A, right) similar to that induced by I$_{K1}$ genetic suppression (personal communication with Dr. H B Nuss). Collectively, these observations indicate that although I$_{K1}$ suppression unleashes latent pacemaker activity of ventricular cardiomyocytes, it is insufficient to reproduce the normal frequency of endogenous nodal pacing.

Figure 9A:
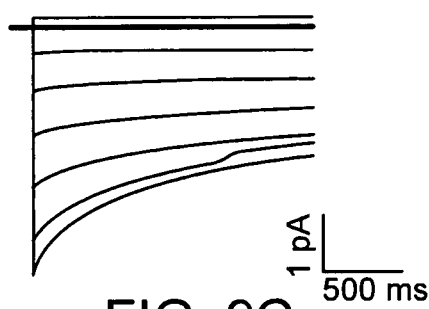
FIG. 9, A thru H are representative illustrations of the effects of HCN2 overexpression in cardiomyoctyes.
Figure 9B:
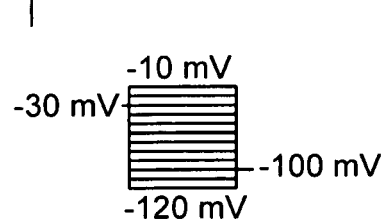
Figure 9C:
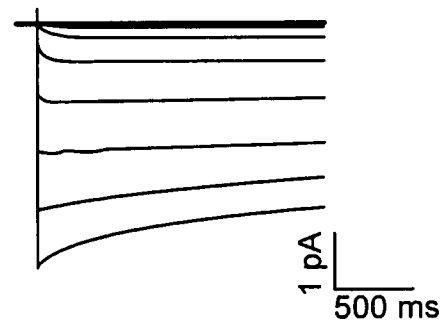
Figure 9D:
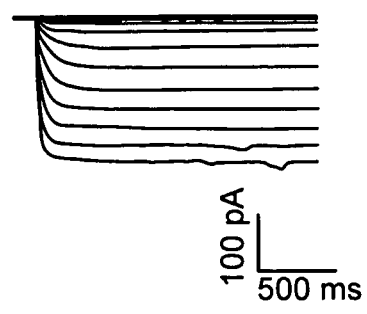
Figure 9F:
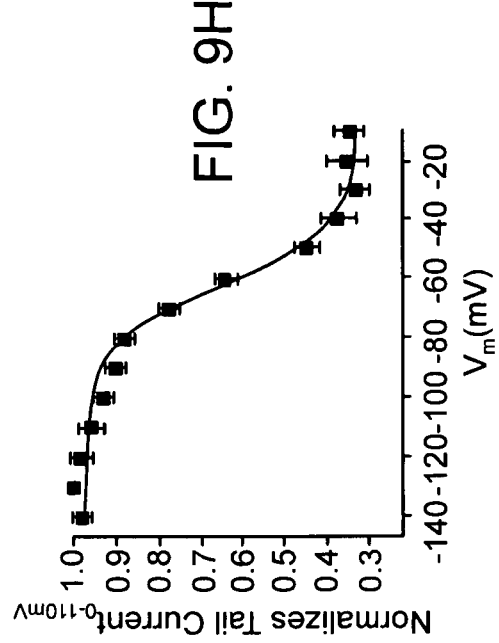
Figure 9E:
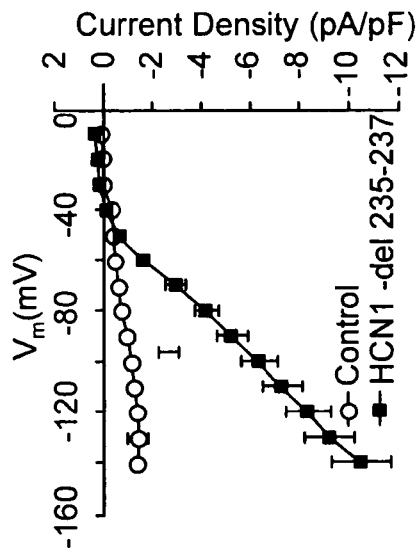
Figure 9H:
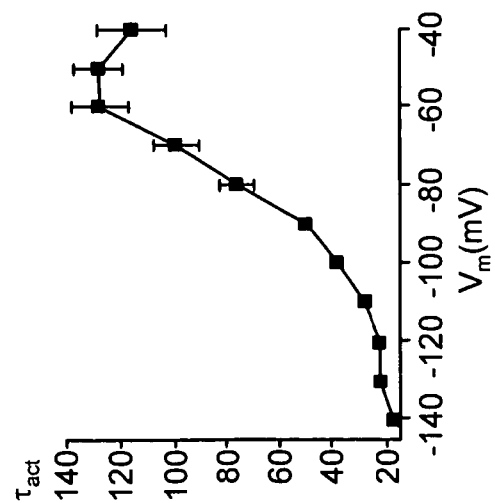
Figure 9G:
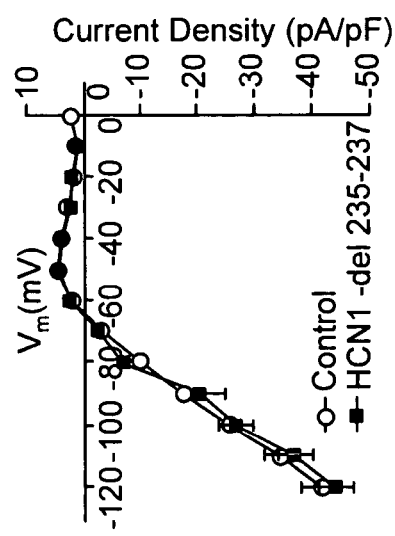

We next investigated the functional consequences of Ad-CGI-HCN1-ΔΔΔ-mediated I$_f$ overexpression in the AP waveform of LV cardiomyocytes. Interestingly, automaticity was exclusively observed in Ad-CGI-HCN1-ΔΔΔ-transduced, even without I$_{K1}$ inhibition (n=6; the same representative cell from FIGS. 9C-D is shown in FIG. 10B), but never in control ventricular cells. The AP-firing rate was 237±12 bpm (cycle length of 256±12 ms), similar to the native heart rate (HR) of guinea pigs and much higher than that induced by either Ba$^{2+}$ or Kir2.1-AAA (p<0.05). Of note, the MDP (−62±2 mV, n=6; p<0.05) was significantly depolarized relative to the RMP of control cells, and associated with a gradual phase-4 depolarization (slope=0.15±0.02 mV/ms, n=6). These properties were typical of genuine nodal I$_f$. Nonetheless, the rapid AP upstroke (V=121±34 mV/ms, n=6) and overshoot observed were indicative of the ventricular origin of these rhythmic "pacemaker-like" cells.

Example 3

The HCN Approach Functionally Substitutes an Electronic Device In Vivo

Figure 11A:
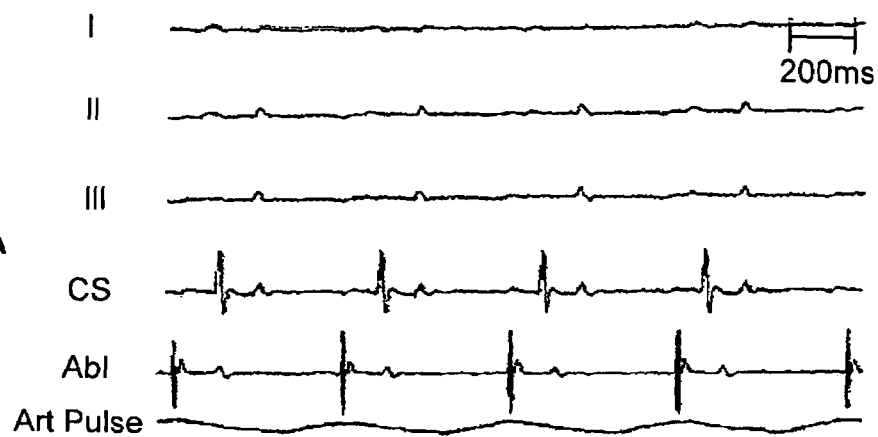
FIG. 11, A thru D are representative illustrations demonstrating, in part, that modified HCN1 can functionally substitute as an electronic device in vivo.
Figure 11B:
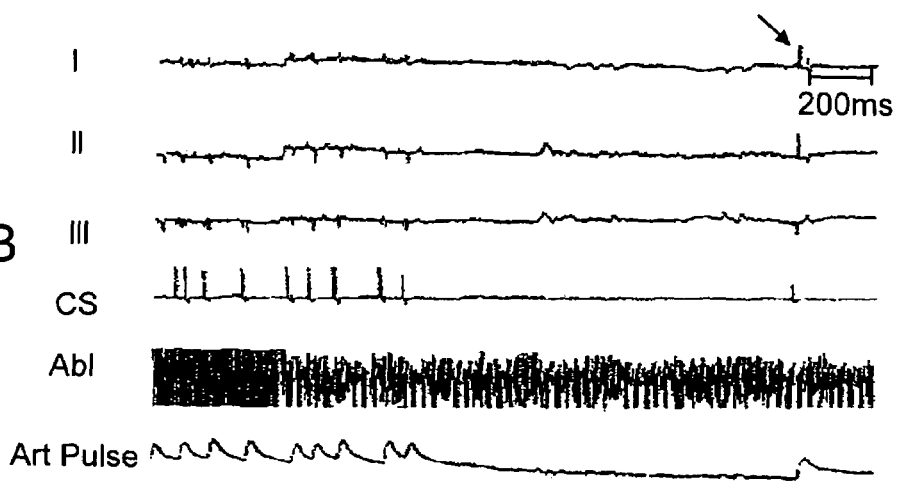
Figure 11C:
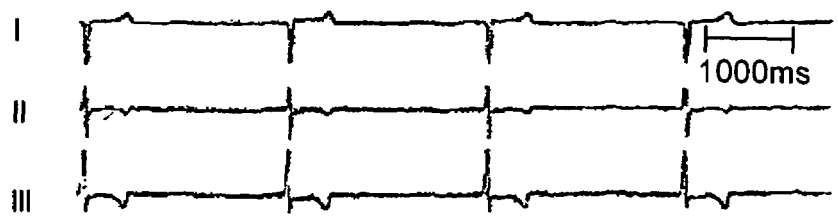
Figure 11D:
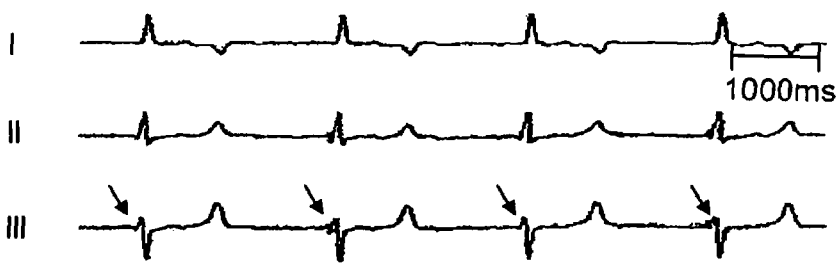

To better test the functional efficacy and therapeutic potential of our gene-based approach in vivo, we next switched to a large animal model. Swines were chosen because they have anatomy and baseline sinus rate (78±14 bpm) similar to those of humans. We first developed a swine model of the SSS by ablating the SA node to cause sinus dysfunction (FIG. 11A-B). To prevent asystole or bradycardias after ablation, we implanted a dual-chamber electronic pacemaker with one electrode positioned at the high anterolateral wall of the RA and another at the right ventricular apex. Electrocardiogram (ECG) recordings after ablation demonstrated the presence of junctional escape rhythm (FIG. 11C) or ventricular pacing rhythm (FIG. 11D) as a result of the implanted device's programmed electrical stimulation when the spontaneous HR fell below 30 bpm.

To further validate our swine SSS model, we closely monitored the heart rhythm of ablated swines for 2 weeks. Indeed, persistent SA node dysfunction was observed in 7 animals: the electronic pacemaker-recorded HR histogram showed that the intrinsic rates were predominantly slower than the lowest programmed rate of 60 bpm and required device-supported atrial electrical stimulations during 87±25% of the period monitored.

Figure 12A:
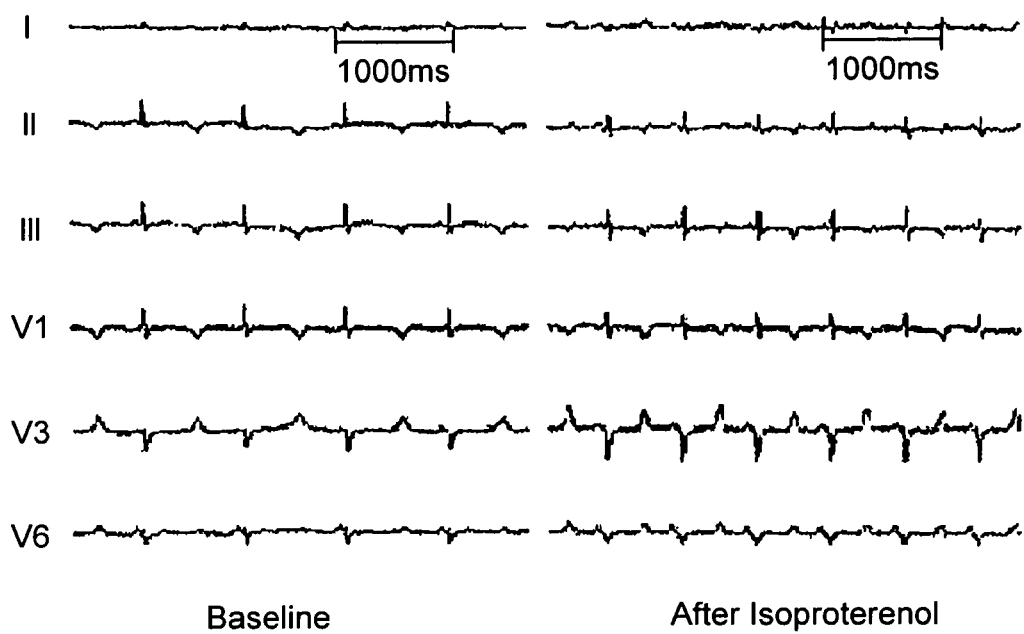
FIG. 12, A thru D are representative illustrations demonstrating, in part, that modified HCN1 can functionally substitute as an electronic device in vivo.
Figure 12B:
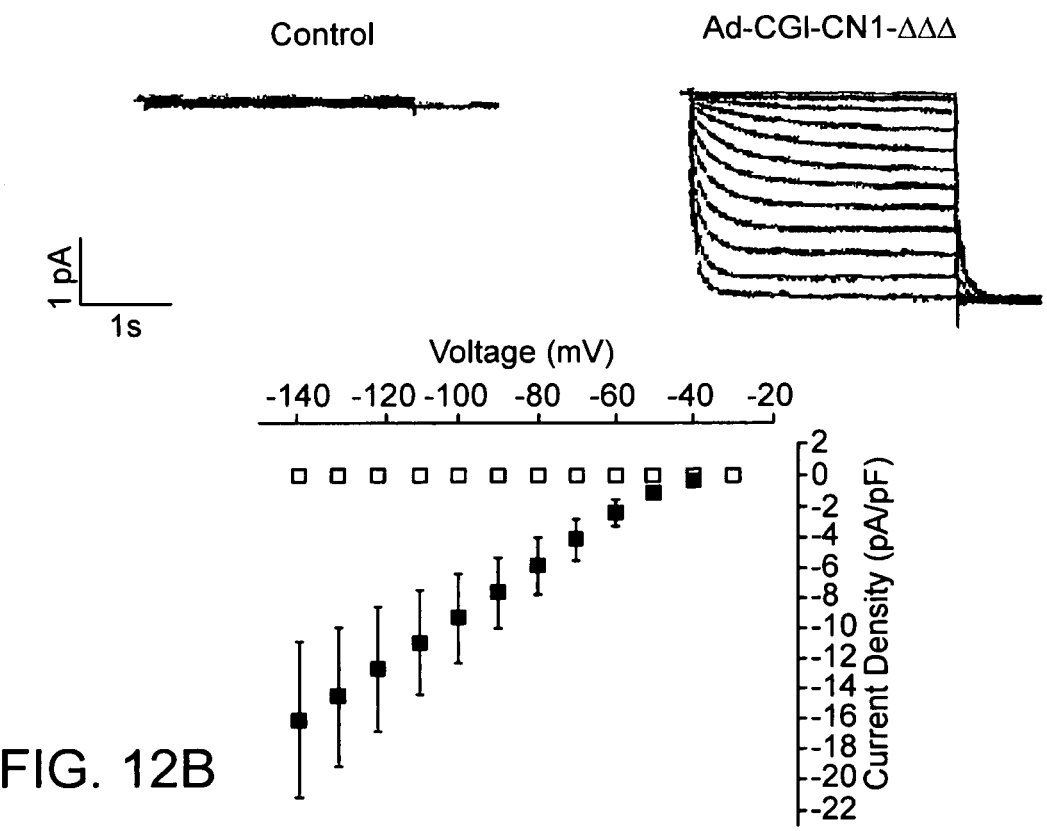

We next injected either Ad-CGI-HCN1-ΔΔΔ (n=3) or saline (n=2) into the LA appendage of these SSS animals. At 10 to 14 days after gene transfer, stable spontaneous atrial rhythms of 64±9 bpm (note the similar P wave morphology on surface ECG) could be detected in Ad-CGI-HCN1-ΔΔΔ-injected SSS animals (FIG. 12A, left). The increased intrinsic HR reduced the need of supportive atrial electrical stimulations to only 27±30%. Interestingly, the spontaneous atrial rhythm increased to 92±10 bpm upon the administration of isoproterenol (1-2 μg/min/kg) (FIG. 12A, right) but not atropine (1.8 mg; data not shown), suggesting that the reverted normal rhythm were not mediated by vagal input but by such locations as the Ad-CGI-HCN1-ΔΔΔ injection site that lacks vagal innervation. Patch-clamp experiments confirmed the overexpression of I$_f$ in Ad-CGI-HCN1-ΔΔΔ-transduced LA cardiomyocytes (FIG. 12B). Neither stable spontaneous atrial rhythm nor I$_f$ was observed in control SSS animals (uninjected, n=2, or those injected with saline, n=2).

Figure 12C:
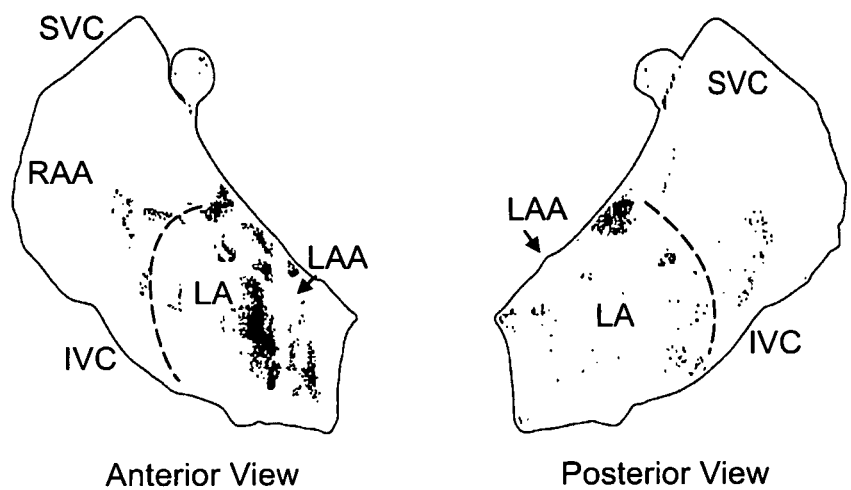
Figure 12D:
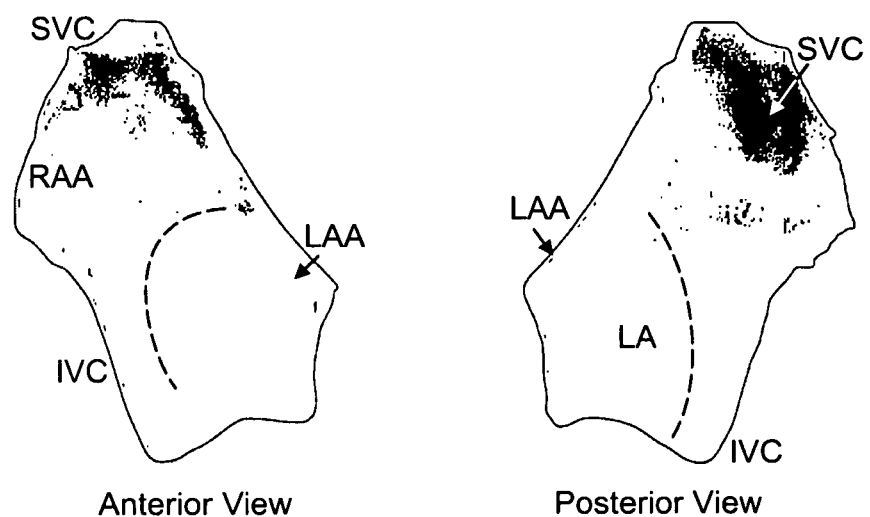

To confirm the precise pacing origin, we investigated the atrial activation pattern of Ad-CGI-HCN1-ΔΔΔ-transduced SSS animals using a non-fluoroscopic electroanatomical mapping technique. For control non-ablated and SSS animals installed with an electronic pacemaker (but injected with saline), endocardial electrical activation was initiated either from the native SA node or the implanted electrode as anticipated (data not shown). By contrast, activation of Ad-CGI-HCN1-ΔΔΔ-injected swines was initiated from the injection site in the LA appendage (red) with the RA activated last (blue-purple) (FIG. 12C). The average atrial endocardial activation time was 101±21 ms. Interestingly, this "reversed" activation pattern reverted to those of controls when mapping was performed with device-driven RA pacing at 10-15 bpm faster than the spontaneous Ad-CGI-HCN1-ΔΔΔ-induced LA rhythm to override the latter effect (FIG. 12D): the earliest electrical activation was once again at the high anterolateral RA, which then propagated to the LA with an activation time of 110±32 ms.

Example 4

Met-232 is Absolutely Required for Channel Functions

Figure 2:
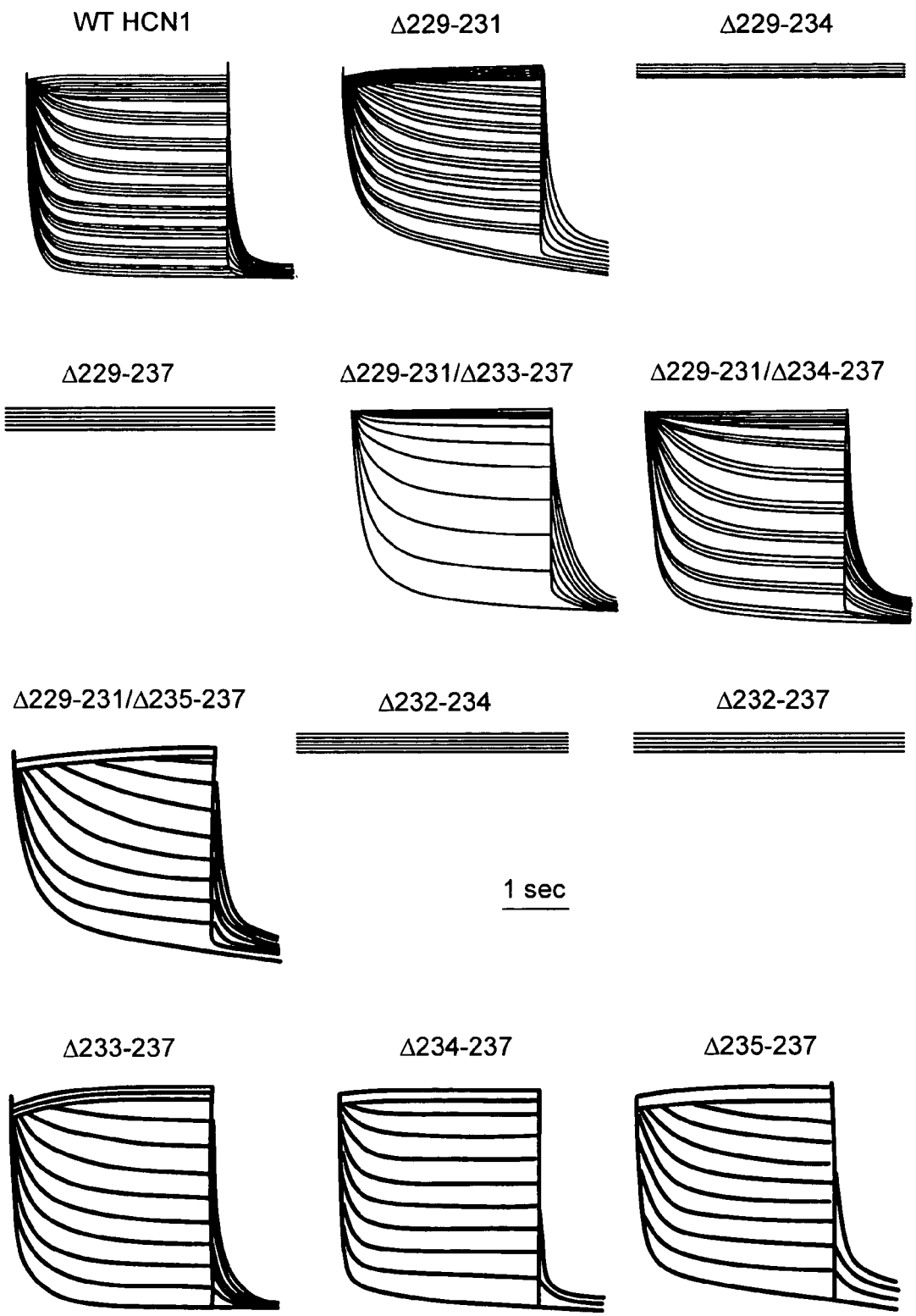
FIG. 2 represents illustrations of the effects of shortening the S3-S4 linker on HCN1 currents; Representative traces of whole-cell currents recorded from cells expressing WT and different deletion HCN1 constructs. Δ229-231, Δ233-237, Δ234-237, Δ235-237, Δ229-231/Δ233-237, Δ229-231/Δ234-237 and Δ229-231/Δ235-237 expressed robust hyperpolarization-activated time-dependent currents. In contrast, oocytes injected with Δ229-234, Δ229-237, Δ232-234, and Δ232-237 produced no measurable currents.
Figure 3:
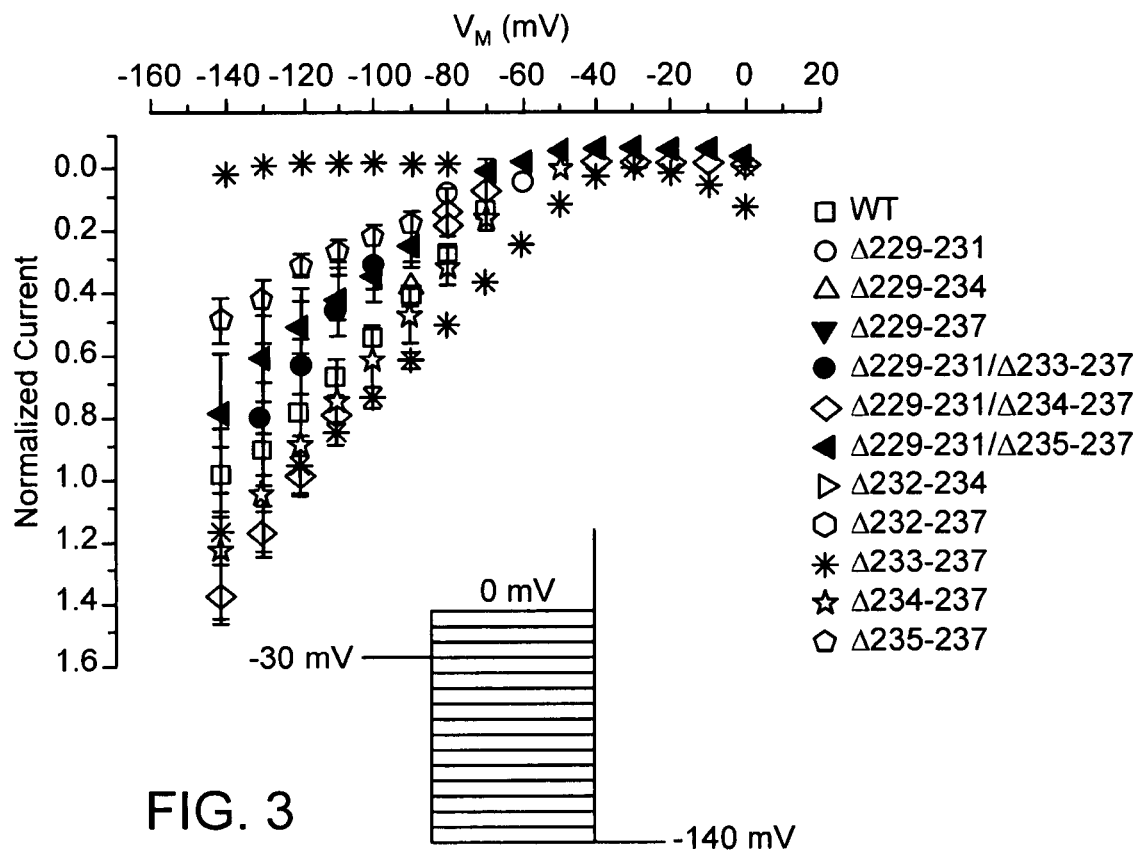
FIG. 3 represents illustrations of the steady-state I-V relationships of S3-S4 deletion constructs. The steady-state current-voltage (I-V) relationship was determined by plotting the HCN1 currents measured at the end of the 3-second pluse. Inset, Electrophysiological protocol used to elicit currents. Data shown are mean±SEM.

To dissect the structural and functional role of the length of the HCN1 S3-S4 linker, we first systematically deleted the linker by different extents (FIGS. 2 & 3). In stark contrast to K$_v$ channels (42), complete deletion of the S3-S4 linker (Δ229-237) did not lead to the expression of functional currents even after hyperpolarization to −140 mV. Similar to Δ229-237, the deletions Δ229-234, Δ232-234, and Δ232-237 also completely abolished normal current activity. To investigate if this loss of channel function due to linker deletion resulted from folding, trafficking or gating defects, we created the fusion constructs HCN1-GFP and HCN1Δ232-234-GFP which contained the green fluorescent protein (GFP) fused to the C-termini of WT and Δ232-234 HCN1 channels, respectively. FIG. 3A shows that GFP fluorescence signals of both HCN1-GFP and HCN1Δ232-234-GFP channels were localized to the membrane surface, suggesting that linker deletions were likely to disrupt gating rather than folding and trafficking. Interestingly, by contrast to the above deletion constructs, all of Δ229-231, Δ233-237, Δ234-237, Δ235-237, Δ229-231/Δ234-237 and Δ229-231/Δ235-237 yielded robust hyperpolarization-activated inward currents. Inspection of their S3-S4 sequences revealed that M232 was common in these constructs (cf. FIG. 1B), suggesting that this linker residue is prerequisite for channels to function. In complete accordance with this notion, Δ229-231/Δ233-237 produced functional channels indicating that loss-of-function due to linker deletion could be rescued by keeping just the single amino acid M232 alone.

Example 5

Effects of Shortening the S3-S4 Linker Length on HCN1 Activation

Figure 4B:
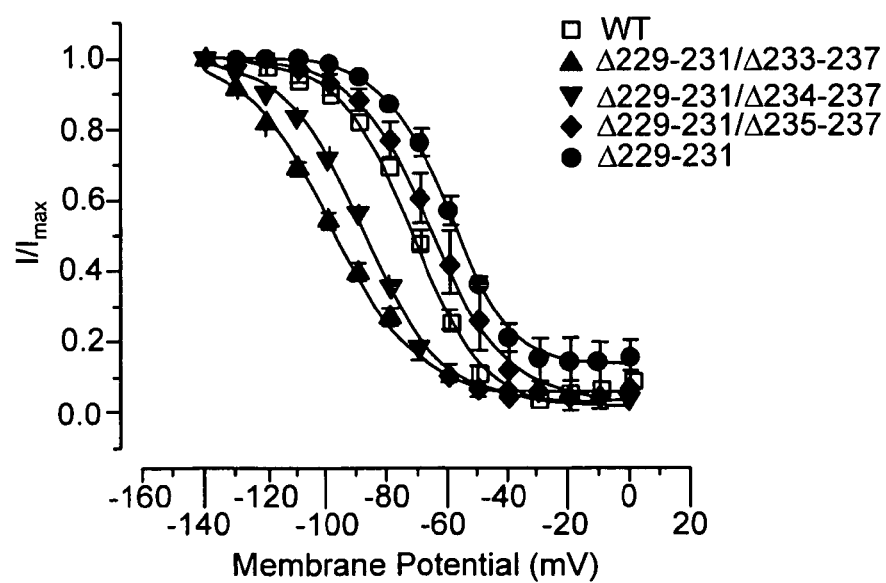
FIG. 4 represents illustrations of the effects of S3-S4 linker deletions on HCN1 steady-state activation. A) Representative tail currents through WT, Δ229-231/Δ233-237, Δ229-231/Δ234-237, Δ229-231/Δ235-237 and Δ229-231 (a, −120 mV; b, −100 mV; c, −80 mV) normalized to the maximum current recorded. B) Steady-state activation curves for WT, Δ229-231/233-237, Δ229-231/234-237, Δ229-231/235-237 and Δ229-231. Increasing the S3-S4 linker length as observed from these constructs, caused sequential depolarizing activation shifts (also see FIG. 8).
Figure 4A:
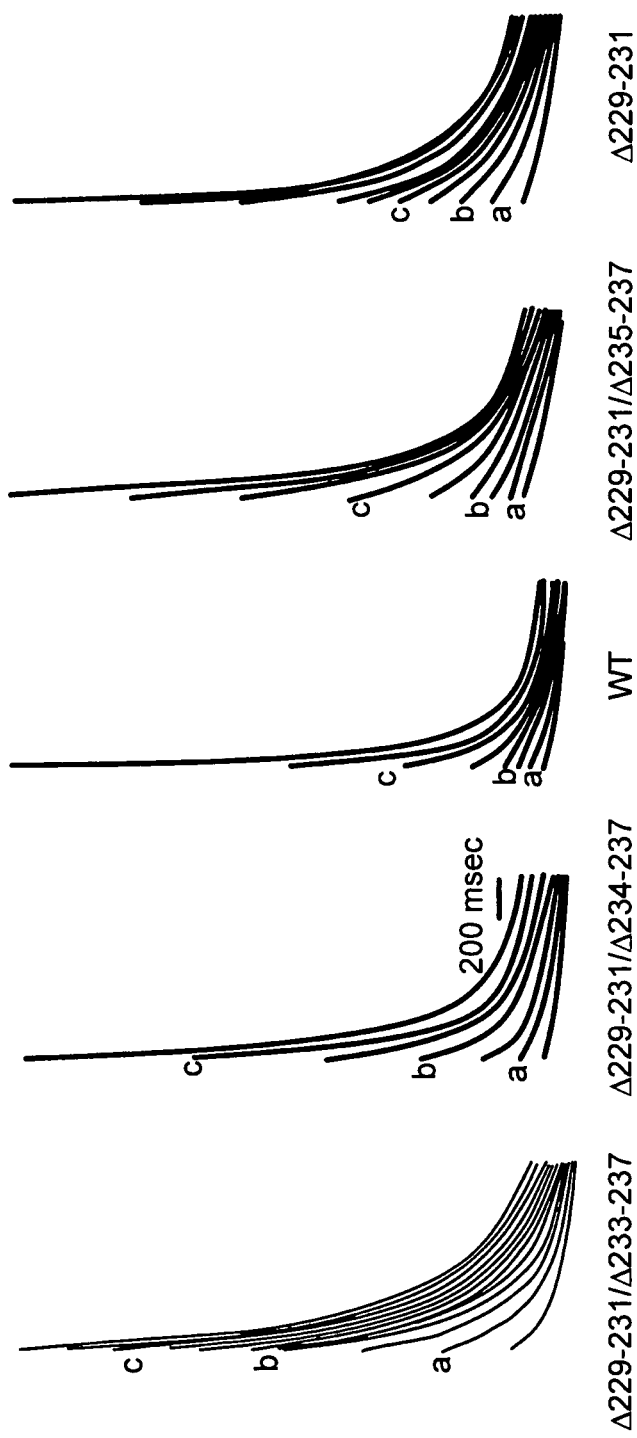
Figure 8:
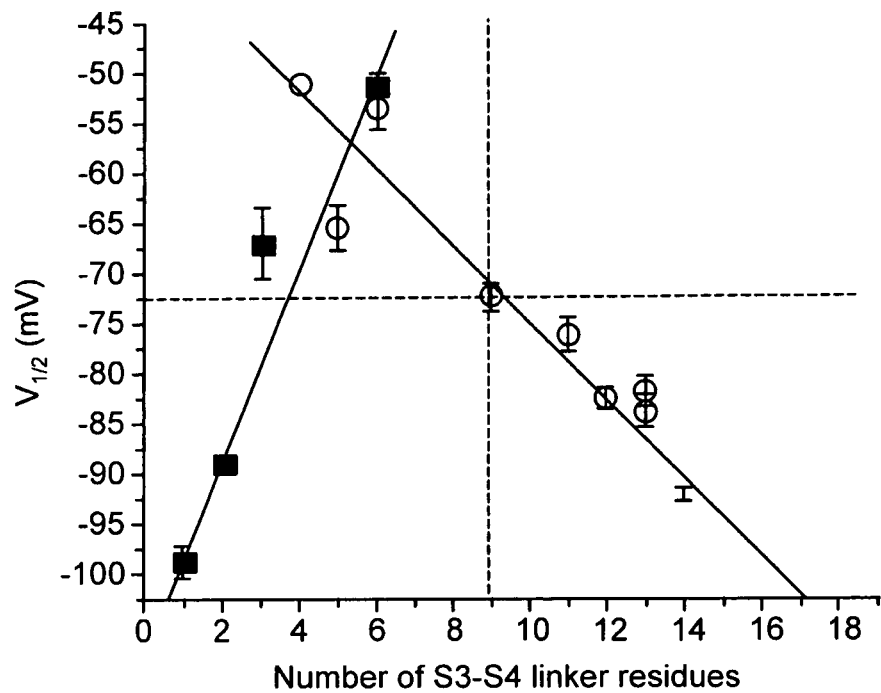
FIG. 8 is a graphic representation summarizing the effects of the S3-S4 linker length on HCN1 steady-state activation. A strong correlation was observed between the $V_{1/2}$ of the channels and their linker length.

The different activation thresholds of our deletion S3-S4 constructs that were functional, as evident from their steady-state current-voltage (IV) relationships (FIG. 3), hint that their activation properties might have been altered. To explore in details the functional effects of linker shortening, we next examined steady-state activation properties (FIG. 4). Δ229-231/Δ233-237 (i.e. only M232 remained) significantly shifted steady-state activation in the hyperpolarizing direction by ~30 mV (vs. deletion of the entire linker rendered channels non-functional). Interestingly, gradual extension of the linker C-terminal to M232 caused progressive depolarizing activation shifts (i.e. Δ229-231/Δ233-237<Δ229-231/Δ234-237<Δ229-231/Δ235-237<Δ229-231; p<0.05). These length-dependent progressive shifts in the Δ229-231 background also appeared to positively correlate to the number of linker residues present (solid squares, FIG. 8; r=0.99). Similarly, restoring the segment containing 229-231 N-terminal to M232 (i.e. Δ233-237) followed the same trend by producing a depolarizing shift. Although the steady-state activation curves of Δ234-237 and Δ235-237 were also positively shifted relative to WT (which contained the complete string of 231-237 residues), the depolarizing effect appeared to have saturated and started to decline when the linker was further prolonged (FIG. 8; also see later). The steady-state gating parameters of our deletion constructs are summarized in Table 1. Taken together, these results strongly suggest that both the length of the S3-S4 linker, in addition to its composition, critically influences HCN1 gating.

TABLE 1

Summary of steady-state activation properties of WT and various S3-S4 mutants.

| Channel | $V_{1/2}$ (mV) | k | N |
|---|---|---|---|
| WT | −72.4 ± 1.4 | 9.8 ± 0.7 | 15 |
| Δ229-231 | −61.2 ± 1.8 * | 9.5 ± 0.7 | 6 |
| Δ229-234 | n.e. | | 5 |
| Δ229-237 | n.e. | | 5 |
| Δ229-231/Δ233-237 | −98.8 ± 1.6 * | 14.5 ± 0.5 * | 5 |
| Δ229-231/Δ234-237 | −88.9 ± 0.4 * | 12.4 ± 0.5 | 10 |
| Δ229-231/Δ235-237 | −66.9 ± 3.6 | 9.3 ± 0.5 | 10 |
| Δ232-234 | n.e. | | 5 |
| Δ232-237 | n.e. | | 5 |
| Δ233-237 | −51.1 ± 1.3 * | 11.6 ± 0.7 | 7 |
| Δ234-237 | −65.4 ± 2.2 | 14.1 ± 0.9 * | 15 |
| Δ235-237 | −53.3 ± 2.3 * | 8.1 ± 0.5 | 5 |
| InsQ233Q | −76.2 ± 1.7 | 12.4 ± 0.7 | 9 |
| InsQQ233QQ | −81.9 ± 1.5 * | 10.8 ± 0.6 | 10 |
| InsQQQ233QQQ | −92.2 ± 0.7 * | 12.7 ± 0.9 | 5 |
| 237InsQQQ | −82.6 ± 0.95 * | 13.4 ± 0.9 | 6 |
| Dup229-232 | −83.8 ± 1.6 * | 11.6 ± 0.7 | 6 |
| Dup229-237 | −104.6 ± 0.5 * | 10.8 ± 0.2 | 9 |

* p < 0.05 Vs WT values; One-way ANOVA followed by Tukey HSD post-hoc test.
n.e. = not expressed Example 6

Figure 5A:
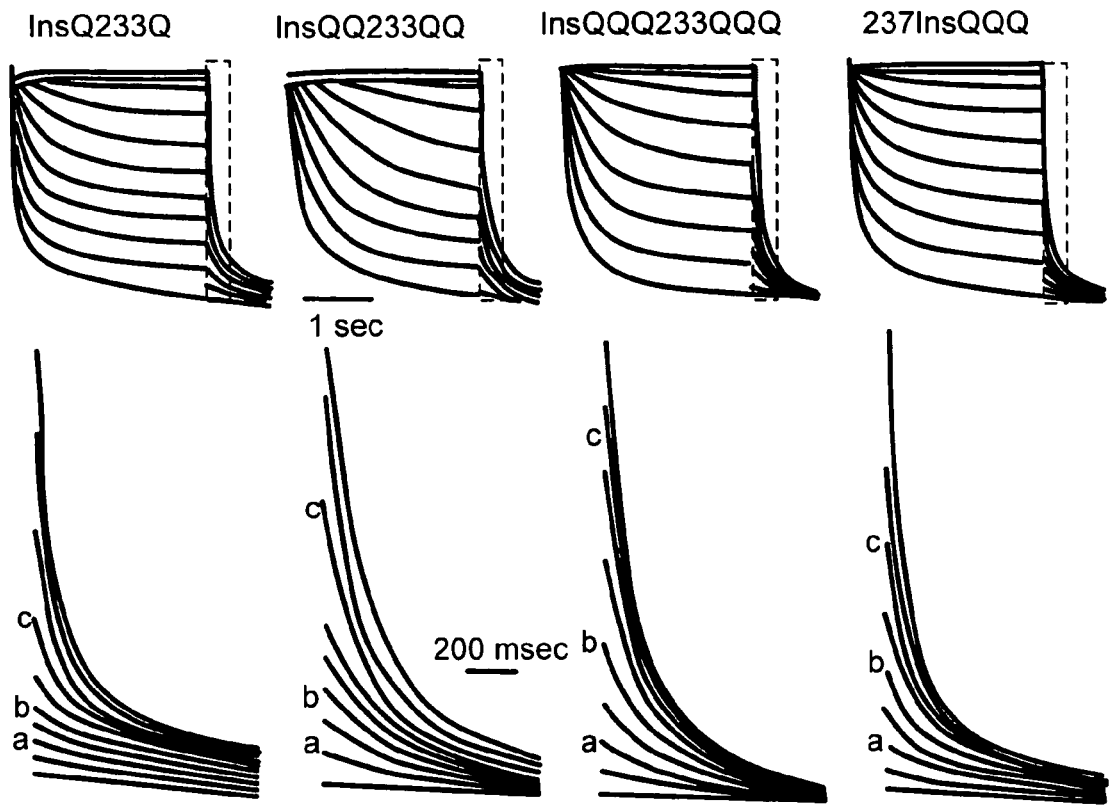
FIG. 5. represents illustrations of the effects of prolonging the S3-S4 linker with glutamines on HCN1 steady-state activation. A) Representative traces of whole-cell currents and their corresponding tail currents recorded from WT, InsQ233Q, InsQQ233QQ, InsQQQ233QQQ and 237InsQQQ channels. a, −120 mV; b, −100 mV; c, −80 mV. B) Steady-state activation curves of the same channels shown in A). Extensive prolongation of the S3-S4 linker shifted activation negatively (see text and FIG. 8).
Figure 5B:
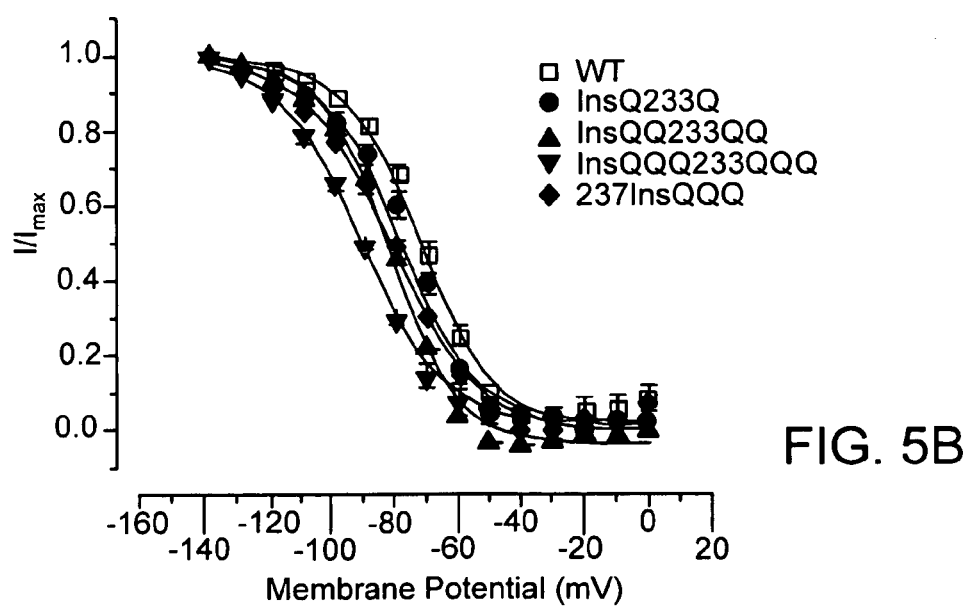

Extensive Prolongation of the S3-S4 Linker Produced Opposite Hyperpolarizing Activation Shifts To complement the above linker deletion experiments, we also studied the effect of prolonging the S3-S4 linker on HCN1 activation gating. Initially, we inserted glutamines to flank D233 to create the insertion constructs InsQ233Q, InsQQ233QQ and InsQQQ233QQQ. D233 was chosen because it faces the opposite side of the critical $GME_{231-235}$ cluster and its substitutions do not affect functions (45). Furthermore, for instance, InsQQQ233QQQ would be expected to displace the original glutamate at position 235 with glutamine without altering the overall linker charge. The effect of Ins237QQQ was also tested. FIG. 5 shows that as the linker prolonged, HCN1 activation progressively shifted in the hyperpolarizing direction (p<0.05).

Figure 6A:
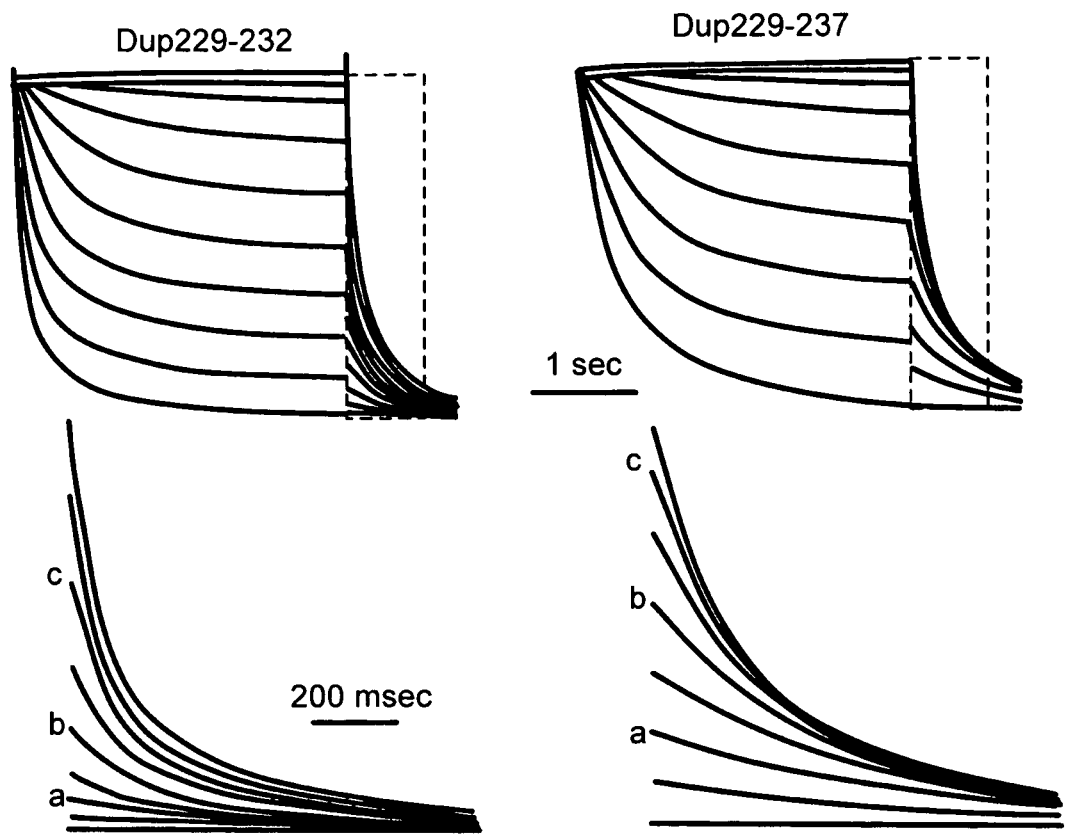
FIG. 6 represents illustrations of the effects of prolonging the S3-S4 linker (i.e. Dup229-232 & Dup229-237) on HCN1 activation. A) Representative whole-cell currents and their corresponding tail currents through WT, Dup229-232 and Dup229-237 channels (a, −120 mV; b, −100 mV; c, −80 mV) normalized to the maximum current recorded. B) Steady-state activation curves. Consistent with the glutamine insertion constructs, the steady-state activation curves of the duplication constructs were also negative shifted. Activation curve of Dup229-237 was more hyperpolarized than that of Dup229-232.
Figure 6B:
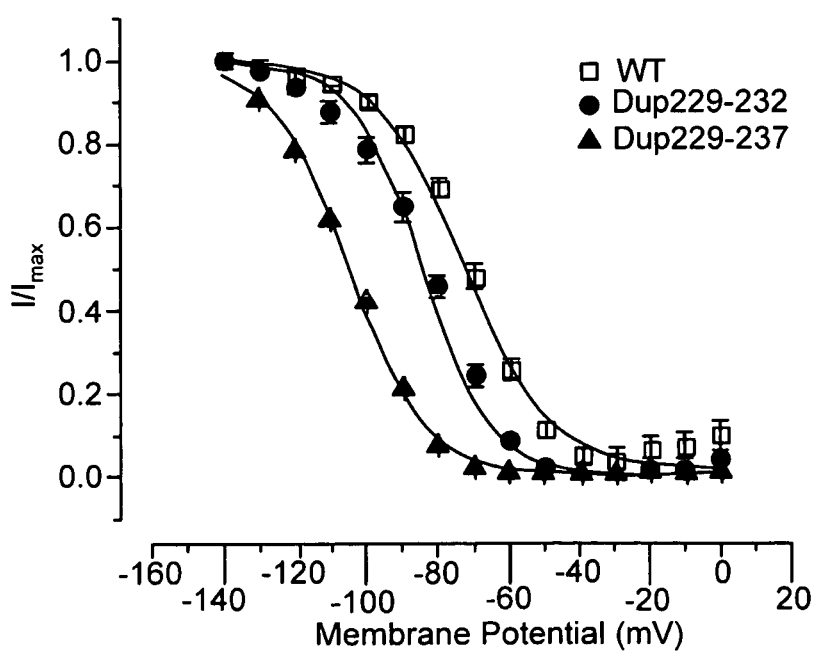
Figure 7A:
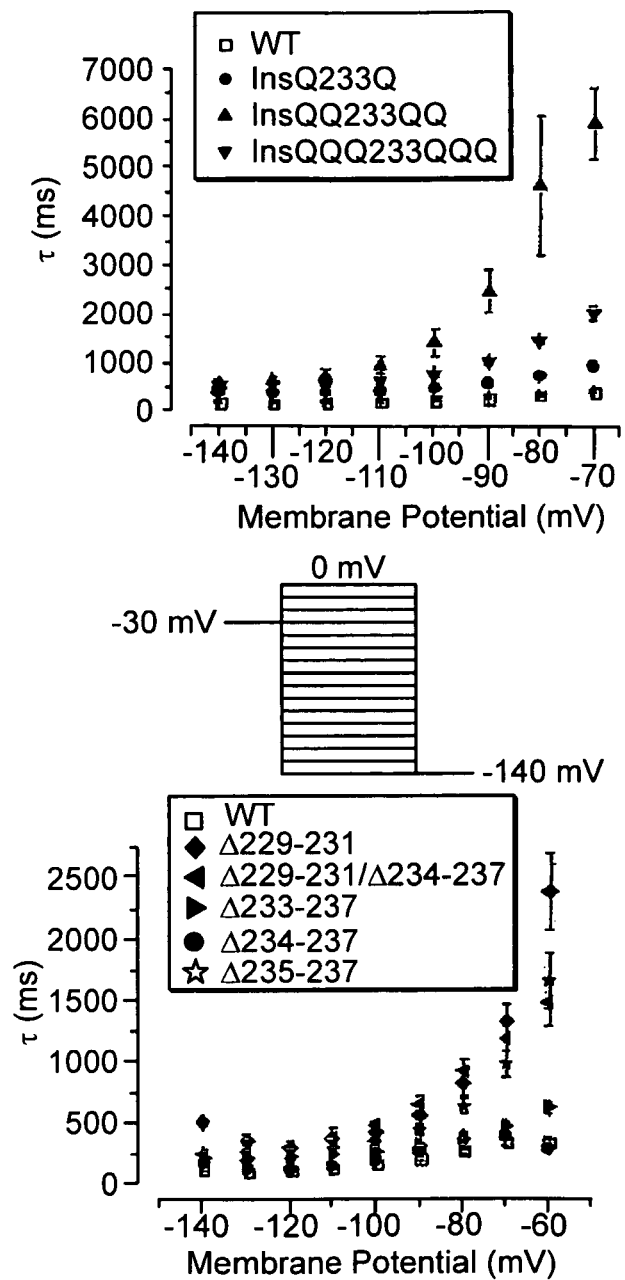
FIG. 7 represents illustrations of the effects of prolonging (top) and shortening (bottom) the S3-S4 linker on activation ($\tau_{act}$) (A) and deactivation ($\tau_{deact}$) (B) kinetics. The electrophysiological protocols used for inducing activation and deactivation are displayed.
Figure 7B:
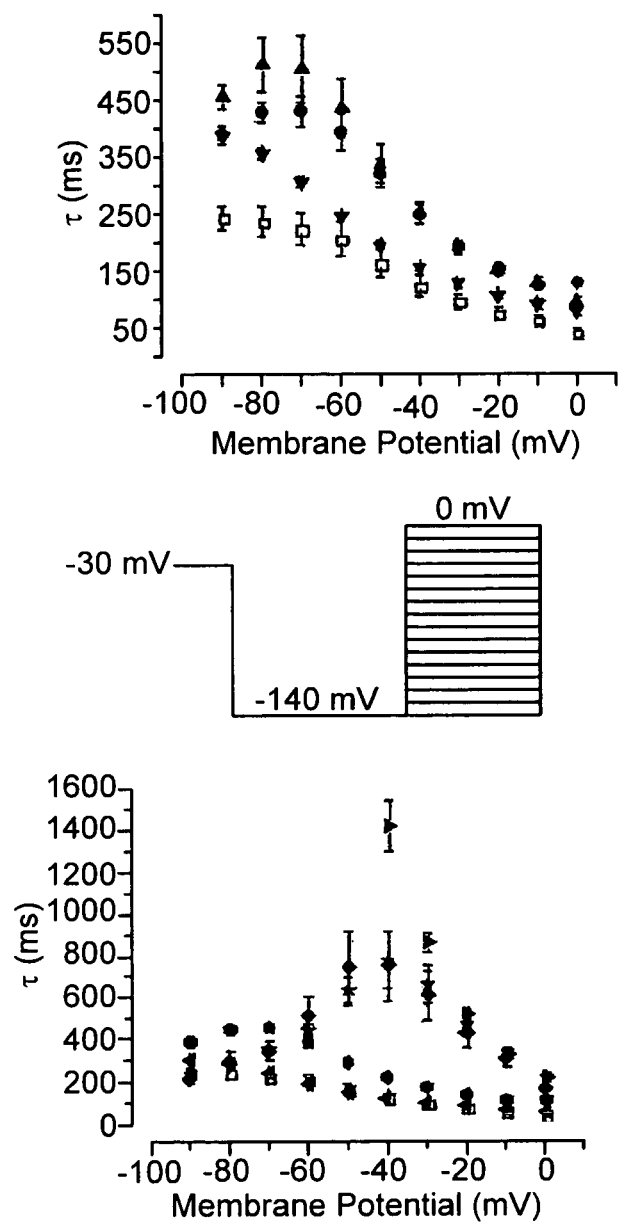

To further test whether the hyperpolarizing shifts resulted from linker prolongation or simply the insertion of glutamines, we duplicated the linker segment containing residues 229-232 as well as the entire linker to create Dup229-232 and Dup229-237, respectively. As shown in FIG. 6, the steady-state activation curves of both duplication constructs were also shifted in the negative direction. In fact, the extent of shifts was also well-correlated to the linker length (open circles, FIG. 8; r=0.98) (after saturation of the depolarizing effect). Table 1 summarizes the steady-state gating parameters of these glutamine and duplication constructs.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

REFERENCES

1. Robinson R B, Siegelbaum S A. Hyperpolarization-activated cation currents: From molecules to physiological functions. *Annu Rev Physiol.* 2003;65:453-480.
2. Gauss R, Seifert R, Kaupp U B. Molecular identification of a hyperpolarization-activated channel in sea urchin sperm. *Nature.* 1998;393:583-7.
3. Ludwig A, Zong X, Jeglitsch M, Hofmann F, Biel M. A family of hyperpolarization-activated mammalian cation channels. *Nature.* 1998;393:587-91.
4. Santoro B, Liu D T, Yao H, Bartsch D, Kandel E R, Siegelbaum S A, Tibbs G R. Identification of a gene encoding a hyperpolarization-activated pacemaker channel of brain. *Cell.* 1998;93:717-29.
5. Santoro B, Tibbs G R The HCN gene family: molecular basis of the hyperpolarization-activated pacemaker channels. *Ann N Y Acad Sci.* 1999;868:741-64.
6. Santoro B, Chen S, Luthi A, Pavlidis P, Shumyatsky G P, Tibbs G R, Siegelbaum S A. Molecular and functional heterogeneity of hyperpolarization-activated pacemaker channels in the mouse CNS. *J Neurosci.* 2000;20:5264-75.
7. Shi W, Wymore R, Yu H, Wu J, Wymore R T, Pan Z, Robinson R B, Dixon J E, McKinnon D, Cohen I S. Distribution and prevalence of hyperpolarization-activated cation channel (HCN) mRNA expression in cardiac tissues. *Circ Res.* 1999; 85:e1-6.
8. Ludwig A, Zong X, Hofmann F, Biel M. Structure and function of cardiac pacemaker channels. *Cell Physiol Biochem.* 1999;9:179-86.
9. Altomare C, Terragni B, Brioschi C, Milanesi R, Pagliuca C, Viscomi C, Moroni A, Baruscotti M, DiFrancesco D. Heteromeric HCN1-HCN4 channels: a comparison with native pacemaker channels from the rabbit sinoatrial node. *J Physiol.* 2003;549:347-59.
10. Ishii T M, Takano M, Ohmori H. Determinants of activation kinetics in mammalian hyperpolarization-activated cation channels. *J Physiol (Lond).* 2001; 537:93-100.
11. Stieber J, Thomer A, Much B, Schneider A, Biel M, Hofmann F. Molecular basis for the different activation kinetics of the pacemaker channels HCN2 and HCN4. *J Biol Chem.* 2003.
12. Seifert R, Scholten A, Gauss R, Mincheva A, Lichter P, Kaupp U B. Molecular characterization of a slowly gating human hyperpolarization-activated channel predominantly expressed in thalamus, heart, and testis. *Proc Natl Acad Sci USA*. 1999;96:9391-6.
13. Ludwig A, Zong X, Stieber J, Hullin R, Hofmann F, Biel M. Two pacemaker channels from human heart with profoundly different activation kinetics. *Embo J*. 1999;18:2323-9.
14. Schulze-Bahr E, Neu A, Friederich P, Kaupp U B, Breithardt G, Pongs O, Isbrandt D. Pacemaker channel dysfunction in a patient with sinus node disease. *J Clin Invest*. 2003; 111:1537-45.
15. Functional heteromerization of HCN1 and HCN2 pacemaker channels: a comparison with native pacemaker channels from the rabbit sinoatrial node. *J Biol Chem*. 2001;276:6069-72.
16. Chen S, Wang J, Siegelbaum S A. Properties of hyperpolarization-activated pacemaker current defined by coassembly of HCN1 and HCN2 subunits and basal modulation by cyclic nucleotide. *J Gen Physiol*. 2001;117:491-504.
17. Xue T, Li R A. An external determinant in the S5-P linker of the pacemaker (HCN) channel identified by sulfhydryl modification. *J Biol Chem*. 2002;277:46233-42.
18. Er F, Larbig R, Ludwig A, Biel M, Hofmann P, Beuckelmann D J, Hoppe U C. Dominant-negative suppression of HCN channels markedly reduces the native pacemaker current I(f) and undermines spontaneous beating of neonatal cardiomyocytes. *Circulation*. 2003;107:485-9.
19. Qu J, Plotnikov A N, Danilo P, Jr, Shlapakova I, Cohen I S, Robinson R B, Rosen M R. Expression and Function of a Biological Pacemaker in Canine Heart. *Circulation*. 2003;107:1106-1109.
20. Nuss H B, Kambouris N G, Marban E, Tomaselli G F, Balser J R. Isoform-specific lidocaine block of sodium channels explained by differences in gating. *Biophys J*. 2000;78:200-10.
21. Miake J, Marban E, Nuss H B. Gene therapy: Biological pacemaker created by gene transfer. *Nature*. 2002;419:132-3.
22. Miake J, Marban E, Nuss H B. Functional role of inward rectifier current in heart probed by Kir2.1 overexpression and dominant-negative suppression. *J Clin Invest*. 2003; 111:1529-36.
23. Lesso H, Li R A. Helical secondary structure of the external S3-S4 linker of pacemaker (HCN) channels revealed by site-dependent perturbations of activation phenotype. *J Biol Chem*. 2003;278:22290-7.
24. Tsang S, Lesso H, Li R A. Dissecting the structural and functional roles of the S3-S4 linker of pacemaker (HCN) channels by systematic length alterations. *J Biol Chem*. 2004.
25. Johns D C, Nuss H B, Marban E. Suppression of neuronal and cardiac transient outward currents by viral gene transfer of dominant-negative Kv4.2 constructs. *J Biol Chem*. 1997;272:31598-603.
26. Hardy S, Kitamura M, Harris-Stansil T, Dai Y, Phipps M L. Construction of adenovirus vectors through Cre-lox recombination. *J Virol*. 1997;71:1842-9.
27. Hamill O P, Marty A, Neher E, Sakmann B, Sigworth F J. Improved patch-clamp techniques for high-resolution current recording from cells and cell-free membrane patches. *Pflugers Arch*. 1981;391:85-100.
28. Qu J, Barbuti A, Protas L, Santoro B, Cohen I S, Robinson R B. HCN2 overexpression in newborn and adult ventricular myocytes: distinct effects on gating and excitability. *Circ Res*. 2001; 89:E8-14.
29. Campbell D L, Giles W R, Hume J R, Shibata E F. Inactivation of calcium current in bull-frog atrial myocytes. *J Physiol*. 1988;403:287-315.
30. Edelberg J M, Huang D T, Josephson M E, Rosenberg R D. Molecular enhancement of porcine cardiac chronotropy. *Heart*. 2001;86:559-62.
31. Melnyk P, Zhang L, Shrier A, Nattel S. Differential distribution of Kir2.1 and Kir2.3 subunits in canine atrium and ventricle. *Am J Physiol Heart Circ Physiol*. 2002; 283: H1123-33.
32. DiFrancesco, D. (1993) *Annu. Rev. Physiol*. 55, 455-472
33. Pape, H. C. (1996) *Annu. Rev. Physiol*. 58, 299-327
34. Gauss, R., Seifert, R., and Kaupp, U. B. (1998) *Nature* 393, 583-587
35. Ludwig, A., Zong, X., Jeglitsch, M., Hofmann, F., and Biel, M. (1998) *Nature* 393, 587-591
36. Santoro, B., Liu, D. T., Yao, H., Bartsch, D., Kandel, E R., Siegelbaum, S. A., and Tibbs, G. R. (1998) *Cell* 93, 717-729
37. Xue, T., Marban, E., and Li, R. A. (2002) *Circ. Res*. 90, 1267-1273
38. Xue, T., and Li, R. A. (2002) *J Biol. Chem*. 277, 46233-46242
39. Männikkö, R., Elinder, F., and Larsson, H. P. (2002) *Nature* 419, 837-841
40. Vemana, S., Pandey, S., and Larsson, H. P. (2004) *J. Gen. Physiol*. 123, 21-32
41. Mathur, R., Zheng, J., Yan, Y., and Sigworth, F. J. (1997) *J Gen. Physiol*. 109, 191-199
42. Gonzalez, C., Rosenman, E., Bezanilla, F., Alvarez, O., and Latorre, R. (2000) *J. Gen. Physiol*. 115, 193-208
43. Gonzalez, C., Rosenman, E., Bezanilla, F., Alvarez, O., and Latorre, R. (2001) *Proc. Natl. Acad. Sci. U.S.A*. 98, 9617-9623
44. Henrikson, C. A., Xue, T., Dong, P., Sang, D., Marban, E., and Li, R. A. (2003) *J Biol. Chem*. 278, 13647-13654
45. Lesso, H., and Li, R A. (2003) *J Biol. Chem*. 278, 22290-22297
46. Tsang, S. Y., Lesso, H., and Li, R. A. (2004)*Biophys. J*. #04-A-3059
47. Santoro, B., Liu, D. T., Yao, H., Bartsch, D., Kandel, E. R., Siegelbaum, S. A., and Tibbs, G. R. (1998) *Cell* 93, 717-729
48. Jiang, Y., Ruta, V., Chen, J., Lee, A., and MacKinnon, R. (2003) *Nature* 423, 42-48
49. Nakai, J., Adams, B. A., Imoto, K, and Beam, K. G. (1994) *Proc. Natl. Acad. Sci. U.S.A*. 91, 1014-1018
50. Catterall, W. A. (1986). *Annu. Rev. Biochem*. 55, 953-985
51. Durell, S. R., and Guy, H. R. (1992) *Biophys. J*. 1, 1-14
52. Xue, T., Marban, E., and Li, R. A. (2002) *Circ. Res*. 90, 1267-1273
53. Xue, T., and Li, R. A. (2002) *J. Biol. Chem*. 277, 46233-46242
54. Azene, E. M., Xue, T., and Li, R. A. (2003)*J. Physiol*. 547, 349-356
55. Sorensen, J. B., Cha, A., Latorre, R., Rosenman, E., and Bezanilla, F. (2000) *J. Gen. Physiol*. 115, 209-222
56. Xue, T., Chan, C. W. Y., Henrikson, C. A., Sang, D., Marban, E., and Li, R. A. (2003) *Circulation* 108, IV-33
57. Xue, T., Azene, E., Henrikson, C., Sang, D., Dong, P., and Li, R. A. (2003) In revision

We claim:

1. A method for modulating the function of a cardiac cell with electrical activity, wherein the cardiac cell otherwise generates electrical signals at an inappropriate frequency, the method comprising administering a polynucleotide construct encoding an HCN1 channel comprising a shortened S3-S4 linker, whereby after administration, the cell generates customized, spontaneous repetitive electrical signals.

2. The method of claim 1, wherein the electrically active cell is a myocardial cell.

3. A method for modulating the function of a cardiac cell with electrical activity, the method comprising administering a polynucleotide construct encoding HCN1 comprising a deletion in any of the amino acid residues between positions 229-237 or any HCN construct that has been modified to exhibit a phenotype different from a wild-type HCN channel whereby after administration, the cell generates customized, spontaneous repetitive electrical signals.

4. The method of claim 3, wherein the methionine at amino acid residue position 232 is not deleted.

5. A method for modulating the function of a cardiac cell with electrical activity, wherein the cardiac cell otherwise generates electrical signals at an inappropriate frequency, the method comprising administering to the cell a adenoviral polynucleotide construct encoding HCN1 comprising an S3-S4 linker comprising a deletion of amino acid residues at positions 235 thru 237, whereby after administration, the cell generates customized, spontaneous repetitive electrical signals.

6. The method of claim 1, wherein expression of the polynucleotide construct provides at least about a ten percent change in the frequency of the electrical signal output of the cells.

7. The method of claim 2, wherein the genetically modified myocardial cell produces customized, spontaneous, rhythmic electrical activity.

8. The method of claim 1, wherein expression of the polynucleotide construct encoding an HCN channel is driven by an inducible promoter.

9. A method for modulating the function of an electrically active cardiac cell, comprising administering a polynucleotide construct encoding an HCN channel comprising a shortened S3-S4 linker to cells that are generating electrical signals at an inappropriate frequency, whereby after administration the cells generate electrical signals at a desired increased or decreased frequency, which is changed from the electrical signal frequency of the cells prior to the administrations.

10. The method of claim 9, wherein the electrically active cells are myocardial cell.

11. A method of treating a mammal suffering from or susceptible to a disease or disorder involving a cardiac cell with undesired electrical activity, comprising administering to the mammal an adenoviral vector comprising a polynucleotide encoding an HCN1 channel comprising a shortened S3-S4 linker, whereby after administration, the cell generates customized, spontaneous repetitive electrical signals.

12. The method of claim 11, wherein the disease or disorder is cardiac arrhythmia.

13. A method for modulating the function of a cardiac cell with electrical activity, the method comprising administering a adenoviral vector comprising a polynucleotide construct encoding HCN1 comprising a deletion in any of the amino acid residues between positions 229-237 or any HCN construct that has been modified to exhibit a phenotype different from a wild-type HCN channel, whereby after administration, the cell generates customized, spontaneous repetitive electrical signals.

14. A method for modulating the function of a cardiac cell with electrical activity, wherein the cardiac cell otherwise generates electrical signals at an inappropriate frequency, the method comprising administering a polynucleotide construct encoding a genetically modified HCN1 channel comprising a shortened S3-S4 linker comprising, wherein the length of the region spanning positions 229-237 of the S3-S4 linker has been altered so that the gating properties of the modified HCN1 are increased or decreased compared to a wild type HCN1, provided that the methionine at position 232 is not deleted, whereby after administration, the cell generates customized, spontaneous repetitive electrical signals, and expression of the polynucleotide construct provides at least about a ten percent change in the frequency of the electrical signal output of the cells.

* * * * *